United States Patent
Campbell et al.

(10) Patent No.: US 12,193,799 B2
(45) Date of Patent: Jan. 14, 2025

(54) IMPLANTABLE MEDICAL SENSOR AND FIXATION SYSTEM

(71) Applicant: Medtronic, Inc., Minneapolis, MN (US)

(72) Inventors: Michael P. Campbell, Blaine, MN (US); George Patras, Greenfield, MN (US); Michael A. Schugt, St. Paul, MN (US); Amir R. Zamiri, New Brighton, MN (US); Richard J. O'Brien, Hugo, MN (US); Ruth N. Klepfer, St. Louis Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 1042 days.

(21) Appl. No.: 16/952,127

(22) Filed: Nov. 19, 2020

(65) Prior Publication Data

US 2021/0068681 A1    Mar. 11, 2021

Related U.S. Application Data

(63) Continuation of application No. 15/378,989, filed on Dec. 14, 2016, now Pat. No. 11,154,207.
(Continued)

(51) Int. Cl.
*A61B 5/021* (2006.01)
*A61B 5/00* (2006.01)
(Continued)

(52) U.S. Cl.
CPC ........ *A61B 5/02141* (2013.01); *A61B 5/0215* (2013.01); *A61B 5/6861* (2013.01);
(Continued)

(58) Field of Classification Search
CPC . A61B 5/02141; A61B 5/0215; A61B 5/6861; A61B 5/6876; A61B 5/6882;
(Continued)

(56) References Cited

U.S. PATENT DOCUMENTS

| 5,103,832 A | 4/1992 | Jackson |
| 5,397,342 A | 3/1995 | Heil, Jr. et al. |

(Continued)

FOREIGN PATENT DOCUMENTS

| CN | 103180008 A | 6/2013 |
| CN | 104203341 A | 12/2014 |

(Continued)

OTHER PUBLICATIONS

First Office Action and Search Report, and translation thereof, from counterpart Chinese Application No. 201680081692.4, dated Apr. 15, 2021 18 pp.

(Continued)

*Primary Examiner* — Jacqueline Cheng
*Assistant Examiner* — Tho Q Tran
(74) *Attorney, Agent, or Firm* — Shumaker & Sieffert, P.A.

(57) ABSTRACT

An implantable medical device, such as a sensor for monitoring a selected internally detectable physiological parameter of a patient, is attached to a fixation assembly that is deployable within the patient to position and orient the sensor to enable it to perform its function. The fixation assembly is formed having at least one flexible asymmetric connector where each fixation member includes a plurality of loops, wherein a first loop of the plurality of loops has a maximum pitch that is different from a maximum pitch of a second loop of the plurality of loops. The attachment of the housing and the fixation assembly includes providing a
(Continued)

tubular member that is welded to the housing and crimped over a section of the fixation assembly.

20 Claims, 13 Drawing Sheets

Related U.S. Application Data

(60) Provisional application No. 62/267,000, filed on Dec. 14, 2015.

(51) Int. Cl.
  *A61B 5/0215* (2006.01)
  *A61N 1/365* (2006.01)
  *A61N 1/375* (2006.01)

(52) U.S. Cl.
  CPC .......... *A61B 5/6876* (2013.01); *A61B 5/6882* (2013.01); *A61B 5/6884* (2013.01); *A61N 1/36564* (2013.01); *A61N 1/3756* (2013.01); *A61B 5/6879* (2013.01)

(58) Field of Classification Search
  CPC ................ A61B 5/6884; A61B 5/6879; A61N 1/36564; A61N 1/3756
  See application file for complete search history.

(56) References Cited

U.S. PATENT DOCUMENTS

| | | |
|---|---|---|
| 6,579,235 B1 | 6/2003 | Abita et al. |
| 7,335,161 B2 | 2/2008 | Von Arx et al. |
| 7,566,308 B2 | 7/2009 | Stahmann |
| 7,572,228 B2 | 8/2009 | Wolinsky et al. |
| 7,792,583 B2 | 9/2010 | Miesel et al. |
| 8,014,874 B2 | 9/2011 | Rossing et al. |
| 8,118,749 B2 | 2/2012 | White et al. |
| 8,777,850 B2 | 7/2014 | Cho et al. |
| 8,864,676 B2 | 10/2014 | Beasley et al. |
| 8,939,905 B2 | 1/2015 | Schugt et al. |
| 9,220,906 B2 | 12/2015 | Griswold et al. |
| 10,307,601 B2 | 6/2019 | Mothilal et al. |
| 2005/0154320 A1 | 7/2005 | Foelich et al. |
| 2006/0200031 A1 | 9/2006 | White et al. |
| 2006/0287602 A1 | 12/2006 | O'Brien et al. |
| 2007/0044393 A1 | 3/2007 | Bonshor |
| 2007/0156057 A1 | 7/2007 | Cho et al. |
| 2007/0270934 A1 | 11/2007 | Stern et al. |
| 2008/0071178 A1 | 3/2008 | Greenland et al. |
| 2008/0243016 A1 | 10/2008 | Liao et al. |
| 2009/0248034 A1 | 10/2009 | Dolan et al. |
| 2010/0185055 A1 | 7/2010 | Robertson et al. |
| 2010/0217135 A1 | 8/2010 | Cho et al. |
| 2012/0029598 A1 | 2/2012 | Zhao |
| 2012/0108986 A1 | 5/2012 | Beasley et al. |
| 2013/0085399 A1 | 4/2013 | Bennett et al. |
| 2014/0275865 A1 | 9/2014 | Tamman et al. |
| 2015/0151121 A1 | 6/2015 | Dagan et al. |

FOREIGN PATENT DOCUMENTS

| | | |
|---|---|---|
| EP | 241294 A | 4/1987 |
| WO | 2009091965 A1 | 7/2009 |
| WO | 2011002564 A1 | 1/2011 |
| WO | 2012090206 A2 | 7/2012 |

OTHER PUBLICATIONS

Bachle, et al., "A systematic review of the influence of different titanium surfaces on proliferation, differentiation and protein synthesis of osteoblast-like MG63 cells," Clin. Oral Impl. Res, 15, pp. 683-692, published 2004, accepted Oct. 30, 2003.

Dasse, et al., "Clinical Experience with Textured Blood Contacting Surfaces in Ventricular Assist Devices," Textured Blood Contacting Surfaces; vol. XXXIII Trans Am Soc Artif Intern Organs, Jul.-Sep. 1987, pp. 418-425.

Jain, et al., "Effect of Titanium Surface Texture on the Cell-Biomaterial Interface," Journal of Investigative Surgery, 16: 263-273, 2003, journal published online Jul. 9, 2009, pp. 263-273.

Frazier, et al., "Immunochemical Identification of Human Endothelial Cells on the Lining of a Ventricular Assist Device," Texas Heart Institute Journal, vol. 20, No. 2, 1993, pp. 78-82. (Applicant points out, in accordance with MPEP 609.04(a), that the year of publication, 1993, is sufficiently earlier than the effective U.S. filing date, so that the particular month of publication is not in issue.).

Swartz, "Literature Review to Support the Addition of Texturing to the Heartware's HVAD® Pump Inflow Cannula," Heartware, wwww.heartware.com, retrieved on or about Nov. 29, 2016 73 pp.

Standard Specification for Unalloyed Titanium, for Surgical Implant Applications (UNS R50250, UNS R50400, UNS R50550, UNS R50700), ASTM International, accessed on Aug. 4, 2016, 5 pp.

Sin, et al., "Surface coatings for ventricular assist devices," Expert Reviews, Medical Devices, 2009; accessed on Aug. 4, 2016, pp. 51-60.

Clubb Jr., et al., "Surface Texturing and Coating of Biomaterial Implants: Effects on Tissue Integration and Fibrosis," ASAIO Journal 1999; Effects of Biomaterial Surface Texturing; accessed on Aug. 4, 2016, pp. 281-287.

International Search Report and Written Opinion from International Application number PCT/US2016/066588, dated Aug. 7, 2017, 13 pp.

International Preliminary Report on Patentability from International Application number PCT/US2016/066588, dated Jun. 28, 2018, 7 pp.

U.S. Appl. No. 15/378,989, Naming Inventors: Campbell et al., filed Dec. 14, 2016.

Prosecution History from U.S. Appl. No. 15/378,989, dated Jan. 4, 2017 through Oct. 21, 2020, 127 pp.

Notice of Allowance from U.S. Appl. No. 15/378,989, mailed Jan. 11, 2021, 9 pp.

Notice of Allowance from U.S. Appl. No. 15/378,989, mailed Jun. 25, 2021, 8 pp.

Corrected Notice of Allowance from U.S. Appl. No. 15/378,989, mailed Sep. 29, 2021, 3 pp.

Second Office Action, and translation thereof, from counterpart Chinese Application No. 201680081692.4, dated Oct. 9, 2021, 12 pp.

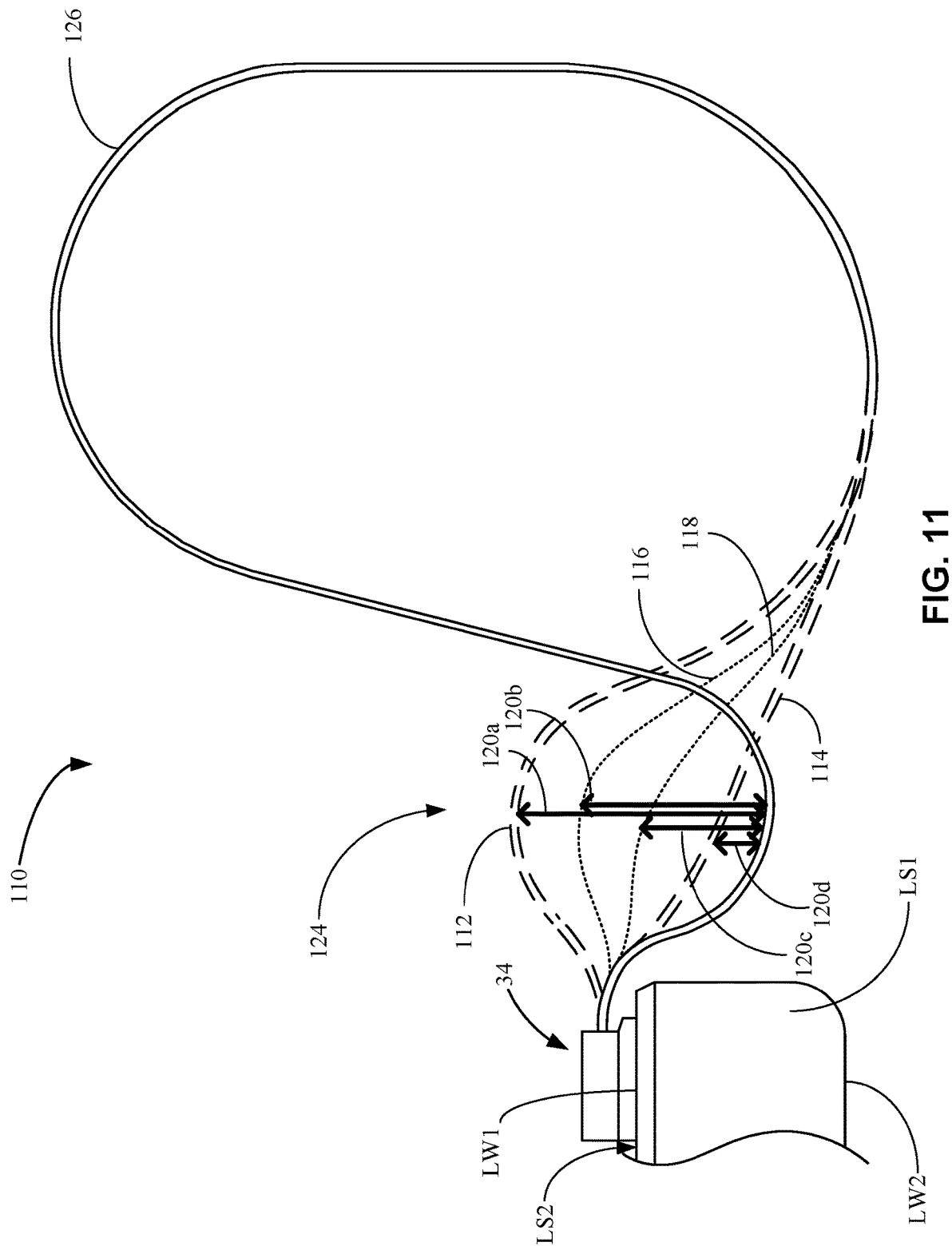

IMPLANTABLE MEDICAL SENSOR AND FIXATION SYSTEM

RELATED APPLICATIONS

This application is a continuation of U.S. application Ser. No. 15/378,989, filed on Dec. 14, 2016 and entitled "IMPLANTABLE MEDICAL SENSOR AND FIXATION SYSTEM," which claims benefit of U.S. Provisional Application Ser. No. 62/267,000, filed on Dec. 14, 2015 and entitled "IMPLANTABLE MEDICAL SENSOR AND FIXATION SYSTEM." The contents of U.S. application Ser. No. 15/378,989 and U.S. Provisional Application Ser. No. 62/267,000 are incorporated herein by reference in their entirety.

BACKGROUND

Various implantable medical devices have been clinically implanted or proposed for therapeutically treating or monitoring one or more physiological conditions of a patient. Such devices may be adapted to monitor or treat conditions relating to heart, muscle, nerve, brain, stomach, endocrine organs or other organs and their related functions. Advances in design and manufacture of miniaturized electronic and sensing devices have enabled development of implantable devices capable of therapeutic as well as diagnostic functions such as pacemakers, cardioverters, defibrillators, biochemical sensors, and pressure sensors, among others. Such devices may be associated with leads to position one or more electrodes or sensors, or may be leadless, with the ability to wirelessly transmit data either to another device implanted in the patient or to another device located externally of the patient, or both.

Although implantation of some devices requires a surgical procedure, other devices may be small enough to be delivered and placed at an intended implant location in a relatively noninvasive manner, such as by a percutaneous delivery catheter. Depending on the nature, function and intended deployment site of the device, the manner in which the device is fixed in place and oriented in the body may affect the operation and accuracy of the device. Consequently, the means by which the device is fixed in place in the body can be a significant factor in its performance and utility.

By way of illustrative example, implantable miniature sensors have been proposed and used in blood vessels to measure directly the diastolic, systolic and mean blood pressures, as well as body temperature and cardiac output. Such direct in vivo measurement of physiological parameters may provide significant information to clinicians to facilitate diagnostic and therapeutic decisions. If linked electronically to another implanted therapeutic device (e.g., a pacemaker), the data can be used to facilitate control of that device. Such sensors also, or alternatively, may be wirelessly linked to an external receiver. As one example, patients with chronic cardiovascular conditions, such as patients suffering from chronic heart failure, may benefit from the use of implantable sensors adapted to monitor blood pressures.

SUMMARY

The disclosure describes implantable medical devices, systems, and associated techniques, structures and assemblies for fixation of the implantable devices within the body of the patient. In an aspect, fixation assemblies are described that provide both appropriate fixation force at the implant site and appropriate strain relief for attachment to the device housing.

The implantable sensor may be coupled to a fixation assembly that includes fixation members that are coupled to opposing ends of the hermetic housing, wherein each of the fixation members includes a multi-loop structure with a plurality of loops. A first loop of the plurality of loops has a maximum pitch that is different from a maximum pitch of a second loop of the plurality of loops. In some examples, each fixation member includes flexible asymmetric loops. The fixation assembly may be formed from a superelastic material and the multi-loop structure is compressible to a delivery configuration that has a narrower profile in relation to a deployment configuration. The multi-loop fixation member includes at least two adjacent loops that are contiguous from a junction in an end-to-end configuration, and at least one of the loops has a different maximum pitch. In some examples, the pitch of each of the loops decreases towards the junction.

In accordance with some examples, an implantable sensor is attached to a fixation assembly of wire-like construction that is compressible to define a delivery configuration and expandable to a deployment configuration. The delivery configuration defines a pitch, width or diameter that is narrower, in relation to the deployment configuration, along a common plane. The implantable sensor includes a housing that is coupled to the fixation assembly in a manner that fixes the position of the implantable sensor relative to the axis of the fixation assembly to prevent the sensor housing from rotating about the fixation assembly.

In some examples, the fixation assembly is dimensioned with respect to the intended deployment site so that when expanded it will contact a portion of the wall of the vessel at substantially diametrically opposed locations in the vessel to sufficiently maintain the positional integrity of sensor at the intended deployment site.

In some examples, the sensor housing may contain pressure sensing components including an externally exposed sensing element and is mounted to the fixation assembly such that, when the fixation assembly is deployed, the sensing element of the sensor will face along a direction generally perpendicular to the plane of the fixation assembly, so as to be disposed in the vessel lumen and be exposed to the blood pressure within the vessel.

In a further aspect, a delivery device for the implantable sensor may include a delivery catheter in which the implantable sensor is mounted in its delivery configuration. The implantable sensor is disposed within the delivery catheter for delivery of the sensor assembly to the implant site. When the delivery catheter has been navigated to the intended implant site, the implantable sensor is deployed so as to expand to the deployment configuration to be in contact with the wall of the implant site and thereby maintain the positional integrity of the sensor at the implant site.

In one example, an implantable medical device (IMD) includes a housing with a power source, a sensing element, and an electronic circuit that is configured to generate a signal indicative of a physiological parameter measured by the sensing element. The housing has first and second opposing ends. The IMD further includes a fixation assembly with asymmetric fixation members coupled to the opposing ends of the housing. Each of the asymmetric fixation members includes a structure with a plurality of loops. A first loop of the plurality of loops has a maximum pitch that is different from a maximum pitch of a second loop of the plurality of loops.

In another example, an implantable medical system (IMD) includes a physiological sensor. The physiological sensor includes a housing with a power source, a sensing element, and an electronic circuit. The electrical circuit is configured to generate a signal indicative of a physiological parameter measured by the sensing element. The housing has first and second opposing ends. The IMD includes a fixation assembly. The fixation assembly has asymmetric fixation members coupled to the opposing ends of the housing. Each of the asymmetric fixation members includes a structure with a plurality of loops. A first loop of the plurality of loops has a maximum pitch that is different from a maximum pitch of a second loop of the plurality of loops. The IMD includes a delivery catheter having an elongate body for delivery of the physiological sensor.

In another example, an implantable medical device, includes a housing having first and second opposing ends. The IMD includes a pressure sensing element on the housing. The IMD includes an electronic circuit within the housing. The electronic circuit may be coupled to the pressure sensing element and configured to generate a signal indicative blood pressure. The IMD includes a fixation assembly with a first asymmetric fixation member coupled to the first opposing end of the housing and a second asymmetric fixation member coupled to the second opposing end of the housing. Each of the asymmetric fixation members includes a structure with a first loop and a second loop. The first loop may be more proximate to the housing than the second loop. The first loop has a maximum pitch less than a maximum pitch of the second loop. Each of the fixation members includes first and second free ends with the first free ends of the fixation members may be oriented in opposing directions relative to one other. The second free ends of the fixation members may be oriented in opposing directions relative to one other.

It should be understood that although the examples described herein principally involve fixing a sensor in a blood vessel, the principles described herein may be used to make implantable sensors assemblies adapted to measure and monitor any of a variety of physiological parameters or to medical devices for delivery of therapy.

BRIEF DESCRIPTION OF THE FIGURES

Throughout the specification, reference is made to the appended drawings, where like reference numerals designate like elements.

FIG. 11 illustrates a side profile view of example arrangements of a fixation member for an example sensor assembly.

DETAILED DESCRIPTION

The present disclosure describes implantable medical devices (IMDs) that sense various physiological parameters of a patient, such as blood pressure. Such IMDs may comprise a fixation assembly and a housing that contains a battery and some electronics. The fixation assembly may interface with the patient to anchor the device in a stable manner to achieve durable sensing parameters. For proper function, the fixation assembly may be configured for delivery through the vascular structure which includes tortuous pathways defined by the blood vessels of the patient. Therefore, there may be a need for the fixation assembly to fit into a delivery system, such as a delivery catheter, for delivery, yet, the same fixation assembly needs to provide an appropriate fixation, once deployed in the body, and survive the long-term mechanical loading at the implant location. In some examples, such as a device having a mechanical pressure sensor, an IiVID may also be configured to reduce the forces that are transferred to a deformable membrane by the fixation.

This disclosure will describe fixation assemblies in the context of a pressure sensing device. However, it should be understood that the fixation assembly may be used in conjunction with other types of devices, such as temperature sensors, cardiac output sensors, or therapy delivery devices such as pacemakers and drug delivery devices.

Figure 1:
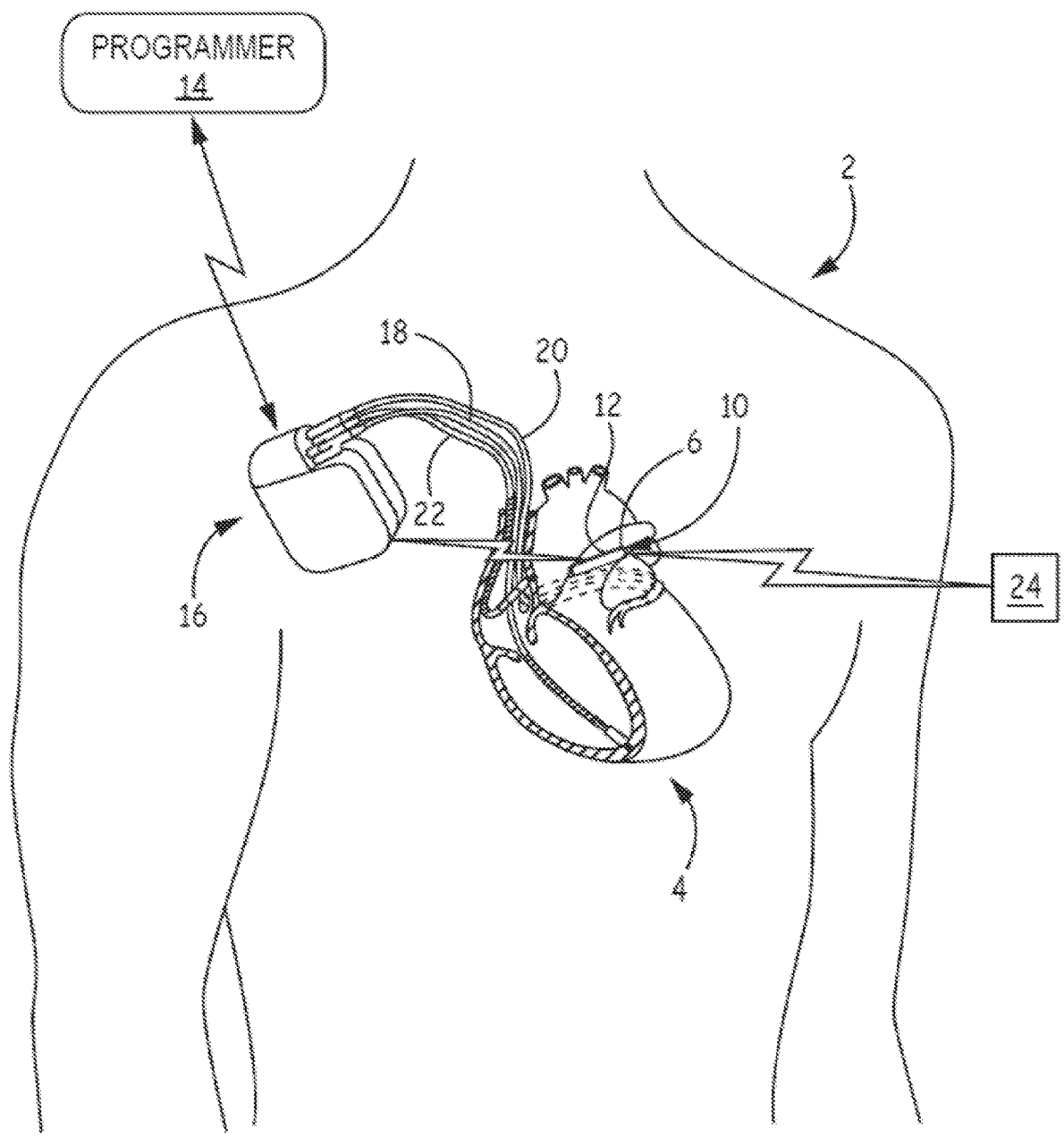
FIG. 1 illustrates, diagrammatically, a patient with example implanted medical devices.

FIG. 1 illustrates, diagrammatically, a patient 2 with implanted medical devices including a sensor assembly 10 implanted, for example, in the patient's pulmonary artery 6 through which blood flows from the heart 4 to the lungs, and another medical device 16, such as a pacemaker, defibrillator or the like. For purposes of this description, knowledge of cardiovascular anatomy is presumed and details are omitted except to the extent necessary or desirable to explain the context of aspects of the disclosure. The device 16 may have one or more leads 18, 20, 22 that are placed in electrical contact with selected portions of the cardiac anatomy in order to perform the functions of the device 16 as are well known to one skilled in the art. The device 16 also may have wireless capability to receive and transmit, by telemetry, signals relating to operation of the device. The device 16 may communicate wirelessly to an external device such as a programmer 14 or to another implanted device such as a sensor 12 of the sensor assembly 10. For the sake of clarity, sensor assembly 10 is shown without a fixation assembly in FIG. 1. The sensor 12 may communicate wirelessly with the programmer 14 or an external receiver 24 to provide in vivo data for selected physiological parameters to an external site to inform clinicians of the patient's status.

Figure 2A:
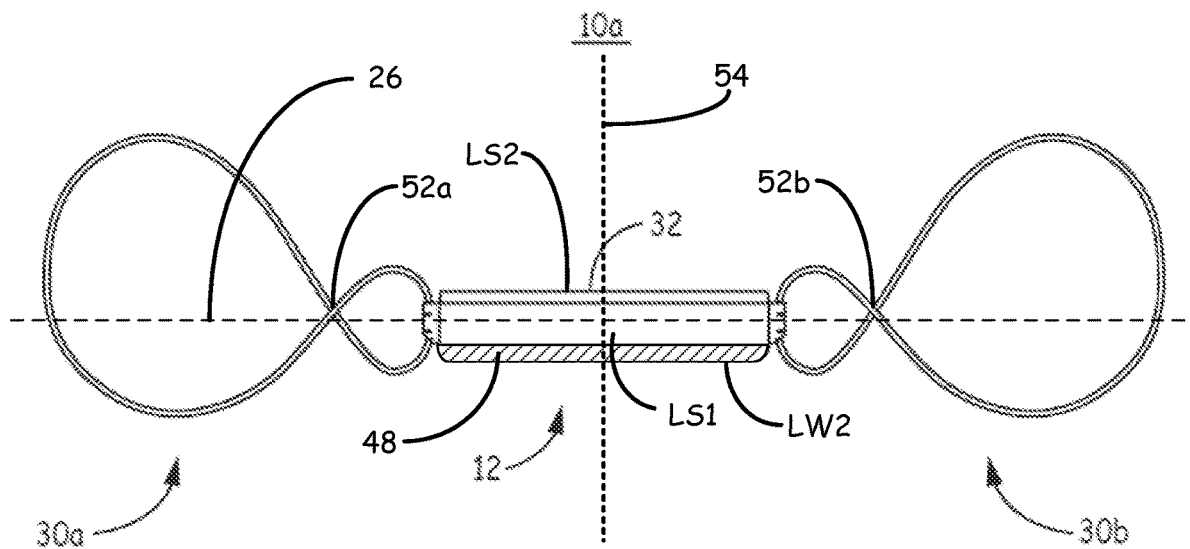
FIG. 2A illustrates a side profile view of an example sensor assembly.
Figure 2B:
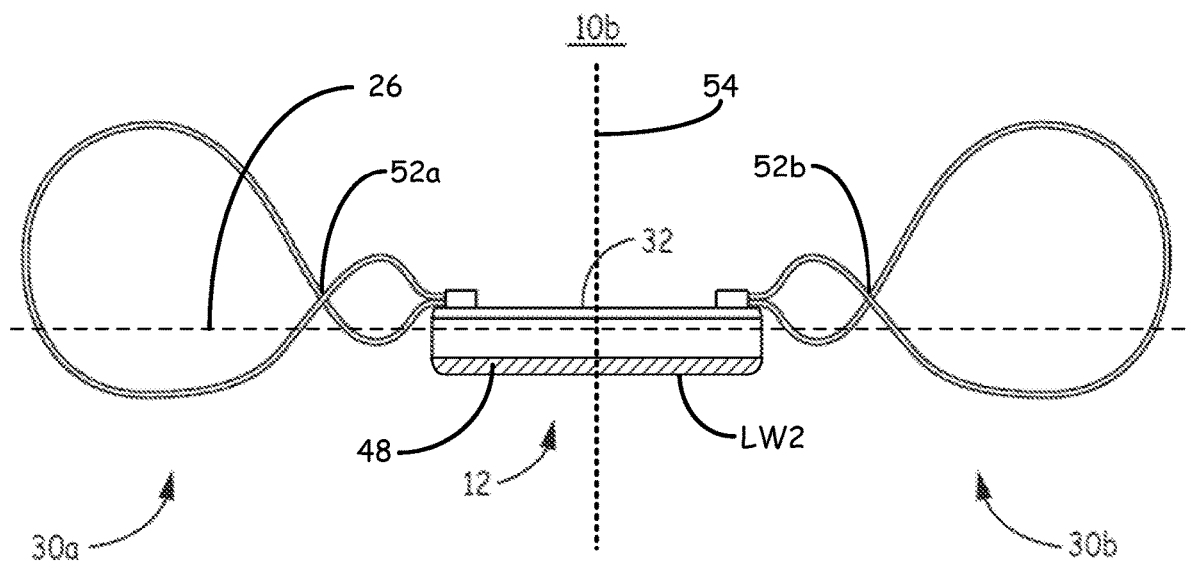
FIG. 2B illustrates a side profile view of an example sensor assembly.

FIGS. 2A, 2B, 3A, 3B, 4A, 4B, 5, 6A, and 6B illustrate examples of sensor assemblies 10 adapted for minimally invasive placement in a patient's blood vessel. The sensor assemblies 10 are depicted in examples of deployment configuration (e.g., rather than being depicted in examples of pre-deployment configuration when sensor assemblies 10 may be in a sheath). Turning first to FIGS. 2A-2B, side profile views of the alternative examples of sensor assembly 10a and sensor assembly 10b (collectively "sensor assembly 10") are depicted. The sensor assembly 10 includes a sensor 12 coupled to fixation members 30a, 30b (collectively "fixation assembly 30"). The fixation assembly 30 and sensor 12 are configured to enable the sensor assembly 10 to be provided in a delivery arrangement that enables the sensor assembly 10 to be navigated to an implant location from which the sensor assembly 10 can be deployed into the deployment configuration.

As described in this disclosure, it should be understood that the delivery configuration of the sensor assembly 10 defines a pitch, width, or diameter that is narrower, in relation to the deployment configuration of the sensor assembly 10 along a common plane. As used herein, delivery configuration may be defined as the general shape of the sensor assembly 10 while being delivered to the blood vessel in a sheath, specifically as the shape relates to the fixation members 30a, 30b. Further, the deployment configuration may be defined as the general shape of the sensor assembly 10 while being delivered to the blood vessel in a sheath, once again specifically as the shape relates to the fixation members 30a, 30b. As used herein, pitch refers to the height that a given loop of the fixation assembly 30 is configured to have in the deployment configuration, as depicted at least in FIGS. 5 and 7A-7C. Put differently, pitch refers to the distance that exists between the opposing wire portions within a given loop in a single plane, wherein the plane is perpendicular to the longitudinal axis 26 of the particular sensor assembly 10. Put yet differently, pitch refers to the length of a line through the central longitudinal axis of a loop, with the line touching two points on opposing edges of each loop, where the central longitudinal axis of the loop may be parallel to the longitudinal axis 26 of the sensor assembly 10.

Upon release/deployment, the fixation assembly 30 expands into the deployment configuration so as to be in physical contact with the wall of the blood vessel to maintain the positional integrity of sensor 12. In one example, the fixation assembly 30 will engage the interior wall of the vessel defining the blood flow lumen. The sensor 12 may be attached to the fixation assembly 30 in a manner such that the sensing element 32 of the sensor 12 is spaced from the wall of the vascular lumen to minimize adverse obstruction to blood flow through the lumen and to position the sensing element 32 of the sensor 12 to be fully exposed to the blood in the vessel, without obstruction from the housing of the sensor or the vessel wall.

In some examples, a bottom longitudinal wall LW2 of the capsule 34 of the sensor assembly 10a may be sintered to promote tissue growth along the bottom longitudinal wall LW2. In such examples, the bottom longitudinal wall LW2 may be sintered as part of a manufacturing step (e.g., the bottom longitudinal wall LW2 may be sintered prior to being assembled within the capsule 34). In other examples, a bottom portion 48 of the sealed housing that includes the bottom longitudinal wall LW2 may be sintered. Sintering the bottom longitudinal wall LW2 of the capsule may reduce strain on the fixation members 30a, 30b (e.g., as a result of the sintering providing some fixation force, the fixation members 30a, 30b may have to provide relatively less fixation forces).

Figure 3A:
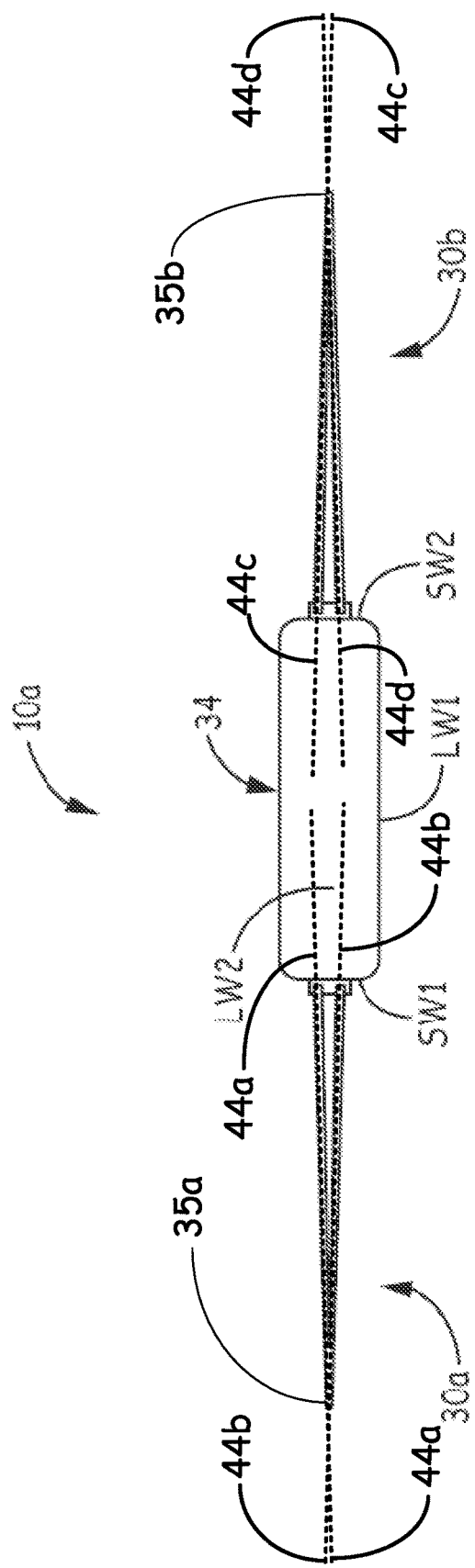
FIG. 3A illustrates a bottom perspective view of an example sensor assembly.
Figure 3B:
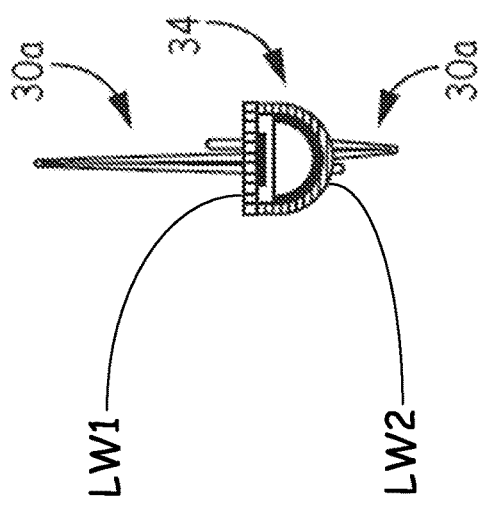
FIG. 3B illustrates a side cross-sectional view of an example sensor assembly.

FIG. 3A illustrates a bottom perspective view of the sensor assembly 10a and FIG. 3B illustrates a side cross-sectional view of the sensor assembly 10a. The features described with respect to sensor assembly 10a and FIGS. 3A and 3B may be included in sensor assembly 10b. The sensor 12 includes a capsule 34 that forms a sealed housing that encloses the operational components such as the electronic circuitry of the sensor assembly 10. In some examples, the sealed housing is hermetically sealed. The capsule 34 defines longitudinal walls e.g., LW1, LW2, that extend from a first lateral side wall SW1 to a second lateral sidewall SW2. The longitudinal walls define the longitudinal axis of the sensor 12. As will be described in more detail with reference to FIG. 4, the fixation members 30a, 30b may be coupled to an exterior of the capsule 34 such as the first and second sidewalls, respectively.

In some examples, the fixation members 30a, 30b may be configured to engage with a vascular wall along a plurality of planes 44a-d (collectively "planes 44"). The fixation members 30a, 30b may expand to occupy the plurality of planes 44 in the deployment configuration after being released from a sheath as described herein. The fixation members 30a, 30b may therein have numerous planes of support upon deployment in the blood vessel, which may result in the sensor assembly 10 being more resistant to "twisting" in a direction generally perpendicular to one of the planes 44 (e.g., more resistant in comparison to an example sensor assembly 10 with a respective fixation assembly 10 that exists along a single plane).

Fixation assembly 30 may apply little more than the force that is appropriate to hold the sensor assembly 10 in place without applying excessive force to that surface. The fixation assembly 30 may be constructed to apply light, but sufficient, force to the vessel. Such forces are at least less than those associated with the placement of vascular stents in which the objective may be to press against the vascular wall with sufficient force to provide scaffolding support for the vessel wall.

Figure 4A:
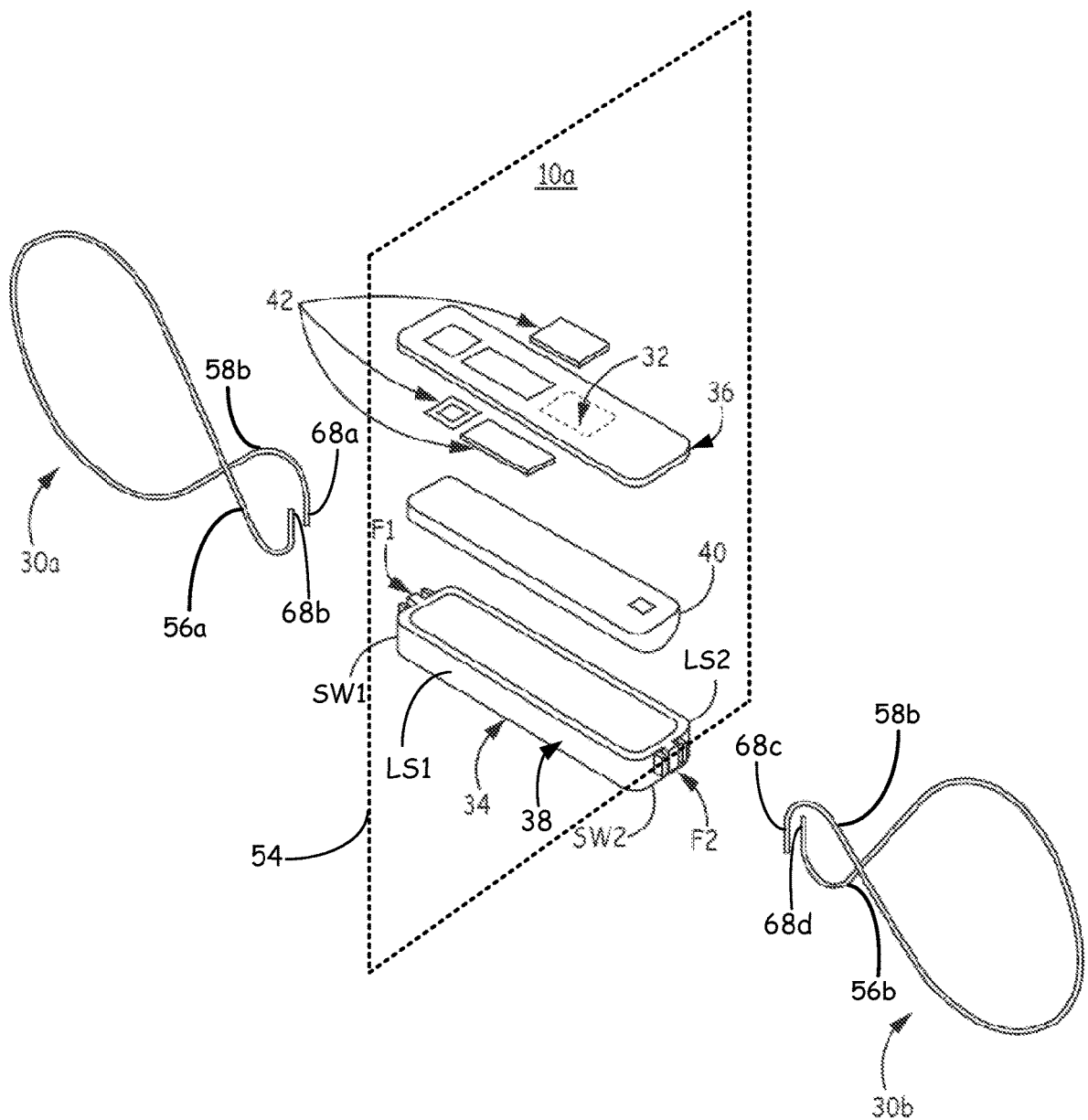
FIG. 4A illustrates an exploded perspective view of an example sensor assembly.
Figure 4B:
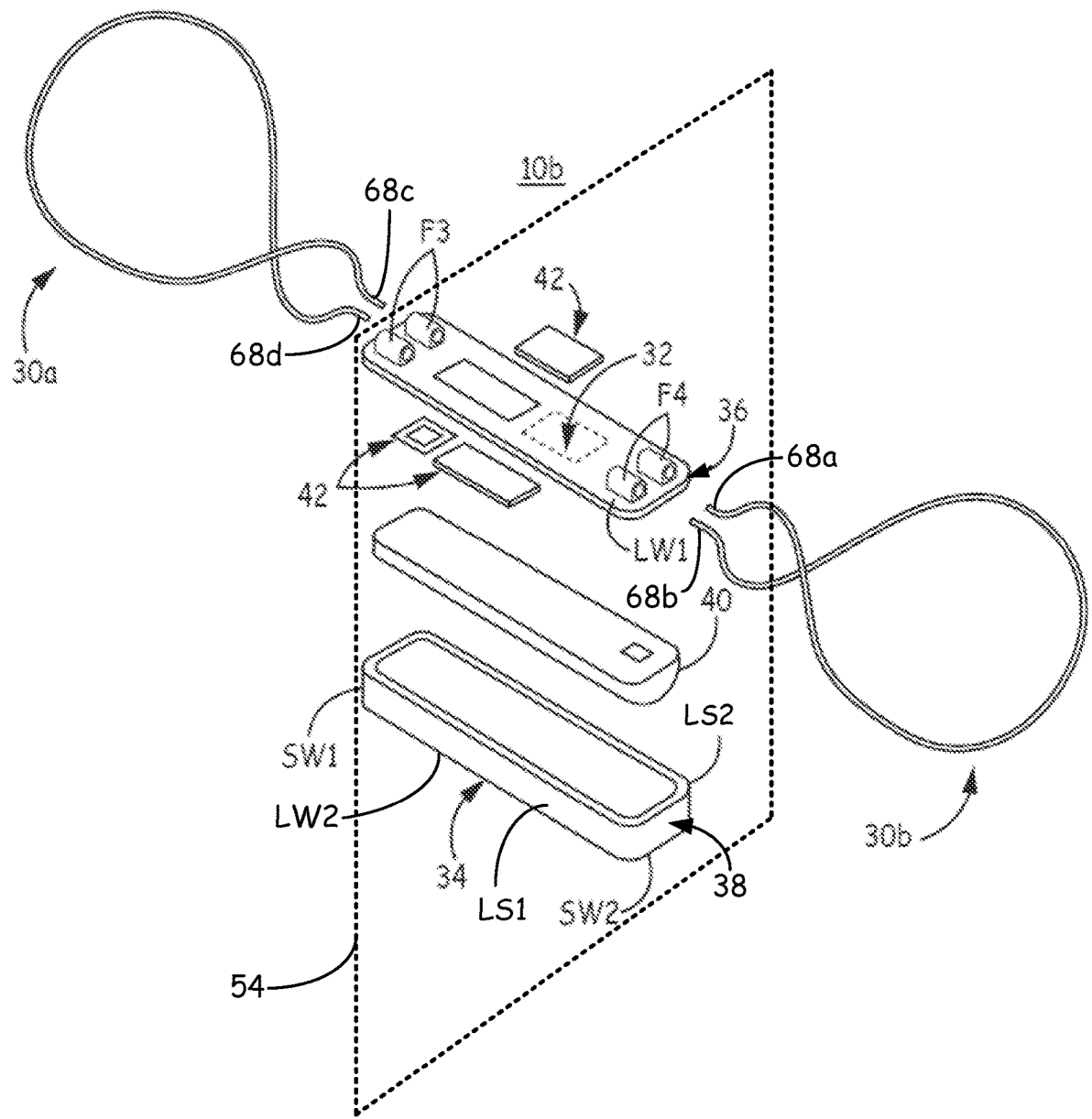
FIG. 4B illustrates a perspective view of an example sensor assembly.

FIGS. 4A and 4B are exploded perspective views of the sensor 12 in accordance with some examples. The capsule 34 may include an elongate body that defines an interior cavity. The interior cavity of the capsule 34 may be sized and shaped to contain the battery 40 and electronics and sensor components 42 of the sensor 12. The capsule 34 may be designed with shapes that are easily accepted by the patient's body while minimizing patient discomfort. For example, the body of capsule 34 may be formed in a cylindrical shape with cylindrical sidewalls. Other non-cylindrical configurations may be employed, however, in which case the corners and edges may be designed with relatively large radii to present a capsule having smoothly contoured surfaces. In the depicted example, the body of capsule 34 may be formed as a generally rectangular structure, which means that the outline of the shape of capsule 34 resembles a rectangle as defined by two lateral side walls SW1, SW2 and two longitudinal side walls LS1, LS2, with contoured edges and corners.

The capsule 34 may be formed having two sections 36, 38. In some examples, one section contains and/or supports the sensing element 32 while the other section contains and/or supports components operably connected to the sensing element. For example, section 36 may contain and/or support a pressure sensing diaphragm of sensor 12 and sensor components 42 while section 38 contains the battery 40.

In some examples, the fixation members 30a, 30b have opposing arrangements as reflected over a central plane 54 of the sensor 12. The fixation members 30a, 30b having opposing arrangements as reflected over the central plane 54 may include specific features of the fixation members 30a, 30b (e.g., a relative rise or dip of a wire along the longitudinal axis 26 of a respective fixation member) being substantially opposite on a relative side of the sensor 12. For example, fixation assemblies 30 may include near portions of wire 56a-b (collectively "near portions of wire 56") that extend axially out from the capsule 34 closer to a first longitudinal side wall LS1 (e.g., closer to the depicted vantage point) than far portions of wire 58a-b (collectively "far portions of wire 58"). Put differently, as used herein, a near portion of wire 56 of a respective fixation member 30 indicates the portion of wire of said fixation member 30 that is in front of a respective far portion of wire 58 of the fixation member 30 as depicted at a juncture 52 (e.g., where a near portion of wire 56 obscures the far portion of wire 58 at the juncture 52). As depicted in FIG. 4A, near portion of wire 56a initially dips as it projects axially out from the capsule 34 before rising to a junction 52, while near portion 56b initially rises as it projects axially out from the capsule 34 before dipping to a respective juncture. Similarly, far portions 58 of the fixation elements 30a, 30b have opposite arrangements as reflected over a central plane 54. In certain examples, fixation members 30a, 30b having opposing arrangements as reflected over a central plane of the sensor 12 may result in load balancing benefits (e.g., as the two fixation members 30a, 30b are configured to stabilize in different directions against different rotations), which may result in a sensor assembly 10 being more stably deposited into a blood vessel.

The capsule 34 may be formed from one or more biocompatible materials that can be sealed (e.g., hermetically sealed) when the sections 36, 38 are joined. A number of such biocompatible materials may be employed, as will be understood by skilled in with the art, including metals and biocompatible plastics. For example, the sections 36, 38 may be formed from unalloyed titanium with an American Society for Testing and Materials (ASTM) grade between 1 and grade 4, or the sections may be formed from an alloyed titanium (e.g., grade 5) that includes aluminum and vanadium. In other examples, section 36 may be formed from a biocompatible mineral, such as sapphire or another variety of corundum. For some examples in which the sections are metal, the metal material of the capsule 34 may optionally be selected to be compatible with the fixation assembly 30 material so as to permit the fixation assembly 30 being securely coupled to the capsule 34. In other examples, the capsule 34 along with the fixation assembly 30 may be integrally formed from one or more of the same or distinct materials. In some examples, the capsule 34, as well as some portions of the fixation member 30, may be encapsulated in a biologically inert dielectric barrier material such as a film of silicone or polyp-xylylene) polymer sold under the trademark PARYLENE.

As shown in FIG. 4A, capsule 34 may include fasteners F1, F2 that define channels for reception of a segment of the fixation assembly 30. In the example of FIG. 4B, capsule 34 may include fasteners F3, F4 that define channels for reception of a segment of the fixation assembly 30. The received segment may include a portion along a length of the fixation assembly 30 or a free end of the fixation assembly 30. The fasteners F1-F4 may be coupled to an exterior of the capsule 34, or in alternative examples, formed integrally with the capsule 34. For example, as shown in FIG. 4A, the fasteners F1, F2 are provided at an exterior of the capsule 34 at the lateral sidewalls SW1, SW2, respectively. In the alternative example within FIG. 4B, the fasteners F3, F4 are provided at spaced apart locations on an exterior of one or more of the longitudinal walls of the capsule 34, such as on the top longitudinal wall LW1, as depicted in FIG. 4B, or alternatively on the bottom longitudinal wall LW2. Spaced apart locations, as used herein, may include four locations on a longitudinal wall LW1, LW2 of the capsule 34, where a first two spaced apart locations are a first distance away from each other on a first lateral sidewall SW1, and the second two spaced locations are mirrored across the central plane 54 of the sensor assembly 10 the first distance away from each other on the second lateral sidewall SW2.

In some examples, the fasteners F1-F4 are formed as pairs of tabs that are arranged to define one or more channel(s) for receiving one or more segment(s) of the fixation assembly 30. Each fastener F1-F4 can include a pair of tabs that are aligned longitudinally as described, for example, in U.S. Pat. No. 8,864,676 to Beasley et al., which is incorporated herein by reference in its entirety. The fasteners F1-F4 may be coupled to the capsule 34 through welding, for example. Alternatively, the fasteners F1-F4 may be formed integrally with the capsule 34. In some examples, the fasteners F1-F4 may be on opposing ends of the capsule 34. It is to be understood that the description of the fasteners F1-F4 is not intended to be limiting, and rather, it is provided to explain the context of aspects of the disclosure.

In the examples depicted in FIGS. 4A-4B, the fasteners F1-F4 are formed as tubular structures that define channels that are sized to receive a segment of each of the fixation members 30a, 30b. In accordance with some examples, the fasteners F1-F4 may be formed as discrete components, such as tubes, for example, that can be coupled to the capsule 34 through coupling techniques such as welding or bonding agent such as glue or crimping. Alternatively, the fasteners F1-F4 may be formed integrally with the capsule 34. As will be described in more detail below, the fixation assembly 30 may be coupled to the fasteners F1-F4 by any suitable coupling technique such as welding, crimping, bonding agent such as glue, or frictional fit.

The channels of fasteners F1-F4 may optionally be defined to receive a segment of the fixation members 30a, 30b in a snug fit arrangement to prevent relative movement between the capsule 34 and the fixation assembly 30. By way of dimensional example, the thickness of a cross section of fixation assembly 30 may be on the order of 0.006 inch for a round shape or 0.0053 inch by 0.012 inch for a rectangular shape. In comparison, the diameter (or width) of the channel of each of the fasteners may be on the order of 0.010 inch to 0.025 inch.

As used herein, free ends 68a-d (collectively, "free ends 68") of a fixation member 30a, 30b may be the two terminating points of the wire of a respective fixation member 30, 30b which may therein each be connected to the capsule 34. The free ends 68 of each of the fixation members 30a, 30b may be oriented in opposing directions. For example, a first free end 68a, 68c may be oriented downward in relation to the lateral sidewall SW1, SW2, while the other ends 68b, 68d may be oriented upward in relation to the lateral sidewalls SW1, SW2 as shown in FIG. 4A. Among other things, such an orientation can provide a degree of load cancellation that minimizes load transfer to the sensing element 32. In alternative examples, one of the fixation members e.g., 30a may be coupled along a lateral sidewall such as SW1 as shown in FIG. 4A, and the other of the fixation members e.g., 30b may be coupled to a longitudinal wall such as LW1 or LW2 as shown in FIG. 4B.

Figure 5:
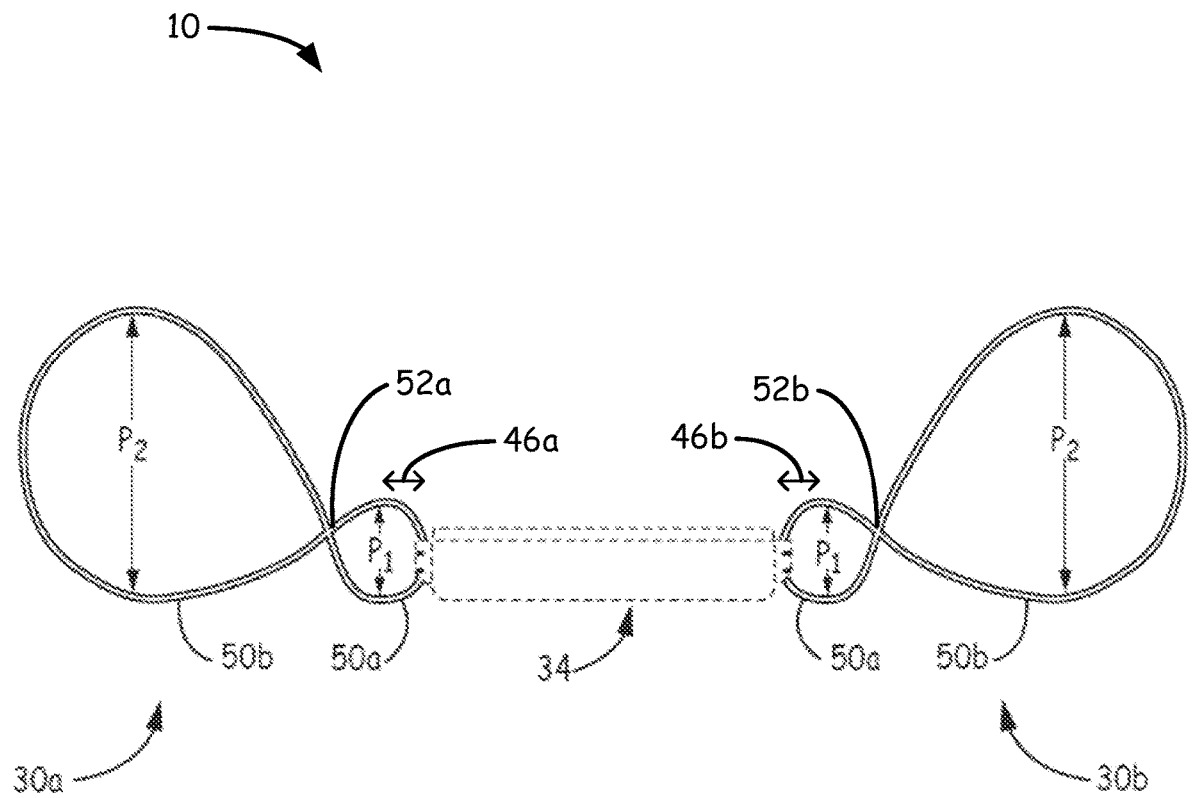
FIG. 5 depicts an example fixation assembly of an example sensor assembly.
Figure 6A:
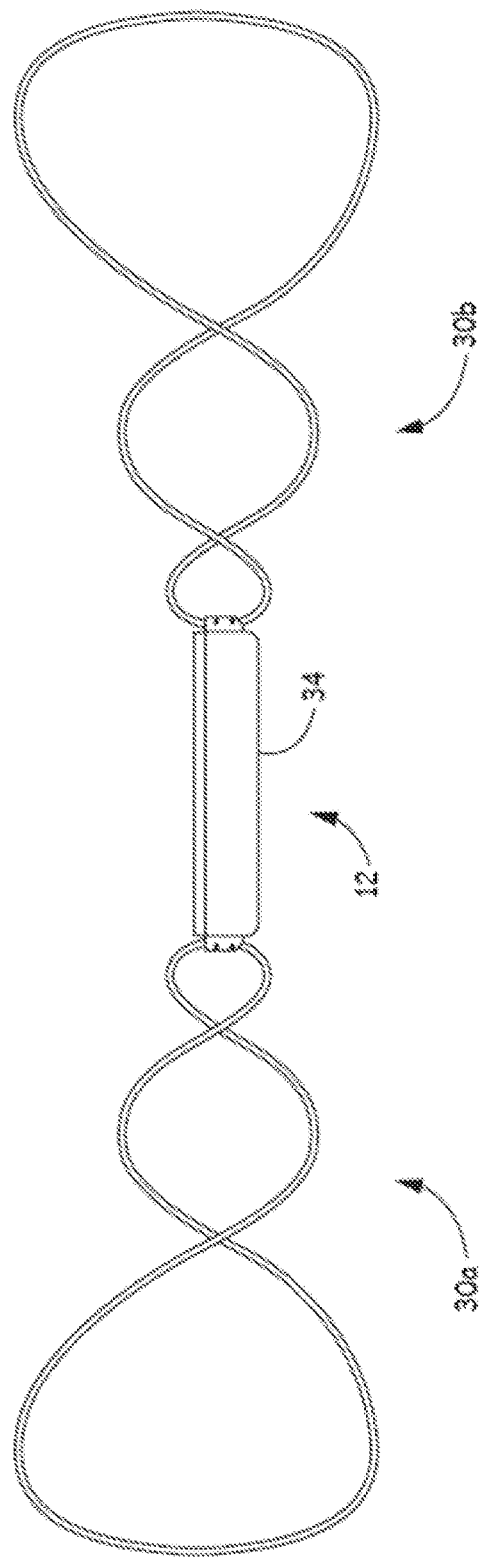
FIG. 6A depicts an example fixation assembly of an example sensor assembly.
Figure 6B:
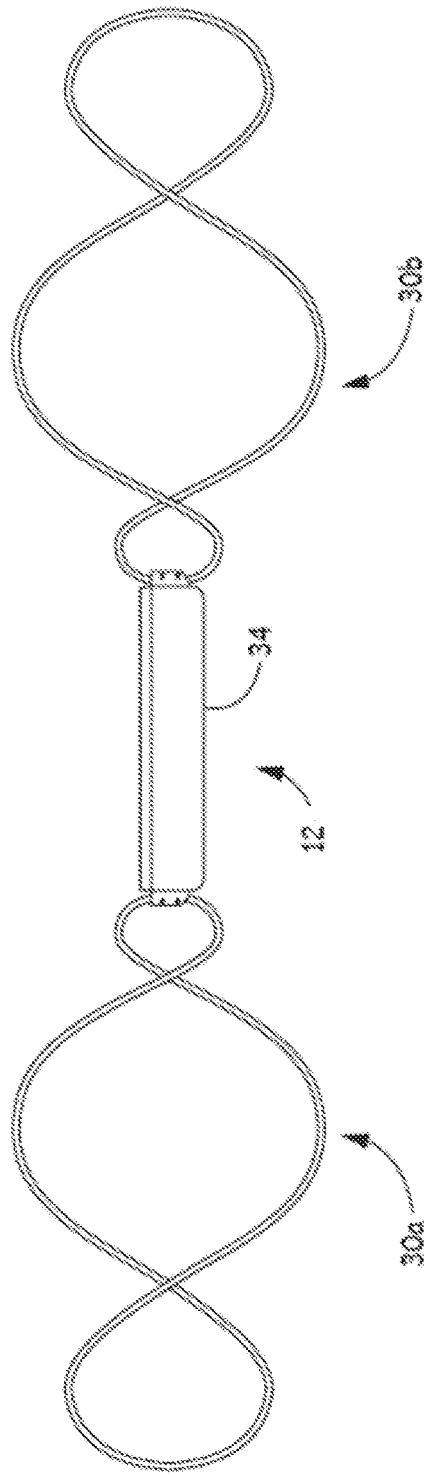
FIG. 6B depicts an example fixation assembly of an example sensor assembly.

FIG. 5 depicts the fixation assembly 30 of the sensor assembly 10. For ease of discussion, the details of sensor 12 are not shown and an outline of the sensor 12 is shown in dashed line. The reader may refer to the foregoing figures in conjunction with the description of FIG. 5. Each of the fixation members 30a, 30b comprises a flexible material and may be configured in a helical configuration in one example. In some examples, for example as depicted at least in FIG. 2A, each of fixation members 30a, 30b may be configured in a double helical configuration Each of the fixation members 30a, 30b may be coupled at opposing ends of the sensor capsule 34. In the illustrated example, the fixation members 30a, 30b are coupled at opposing lateral sidewalls of capsule 34 (e.g., as depicted with respect to 10a and 2a) The configuration of 30a, 30b, depicted and described with respect to FIG. 5 may be equally applicable to other example locations of the attachment of the fixation structures to capsule 34, such as attachment to of fixation members 30a, 30b to top longitudinal wall LW1 as depicted in FIG. 2b. In some examples, the fixation assembly 30 may be formed from a highly elastic material capable of "remembering" a first shape, such that even when the fixation assembly 30 is condensed to a second, smaller shape (e.g., when the fixation assembly 30 is inside a sheath) the fixation assembly 30 may return to the first shape when no longer so condensed (e.g., when removed from the sheath). For example, the fixation assembly 30 may be formed from a highly elastic biocompatible alloy capable of forming stress induced martensite (SIM). Nitinol (TiNi) is an example of such materials that are also referred to as being "pseudoelastic" or "superelastic." Each of the fixation members 30a, 30b can be formed into a single, integral component.

In some examples, the fixation members 30a, 30b may be formed from a wire-like element that is configured into the desired shape. Such wire-like elements may comprise a linear element having any desired cross-section such as round or rectangular. In other examples, the fixation members 30a, 30b, may be formed from a sheet of material by laser cutting or electrochemical etching or other fabricating techniques known in the art. Regardless of the construction method, each of the resulting fixation members 30a, 30b may have a substantially uniform thickness. As used in this disclosure, the term substantially uniform thickness means that the thickness dimension along a length of the members 30a, 30b is constant or is within a variation of up to 15%.

Each one of the fixation members 30a, 30b may be configured to define a pair of longitudinally spaced asymmetric loops 50a, 50b formed in a helical configuration when attached to capsule 34. The asymmetric loops 50a, 50b are formed in an end-to-end configuration so as to intersect or overlap at junctions 52. It should be understood that the asymmetric loops 50a, 50b need not be in contact at the junctions 52 (e.g., as a result of being in different planes 44 to have numerous planes 44 of support as discussed herein), but rather, that they may overlap as viewed from the side to form a helical configuration as shown in the perspective view of FIG. 3. Stated another way, the cross section of the structure of each of the fixation members 30a, 30b may generally resemble the number "8" in some examples when viewed from a side profile. Moreover, although two loops are depicted, the fixation members 30, 30b may include multi-loop structures including three or more loops as depicted, for example, in FIGS. 6A, 6B.

A length of the fixation members 30a, 30b may be contiguous. Alternatively, a length of the fixation members may be detached around a perimeter of one of the loops away from the junction. It should be understood that either one or both fixation members 30a, 30b may be contiguous or detached around the perimeter. A fixation member 30a, 30b that is detached may include two discrete portions of wire that are each individually coupled to the capsule 34 in a manner consistent with this disclosure. A fixation member 30a, 30b that is detached may maintain substantially similar shapes as other fixation members 30a, 30b discussed herein. Fixation members 30a, 30b that are detached may have "breaks" 35a-35b (collectively "breaks 35") at a location furthest away from the capsule 34 along the longitudinal axis 26 as depicted in FIG. 3A. For example, in a fixation member 30a, 30b that is detached, a far portion of wire 56a may not be part of the same wire as near portion of wire 56b, but instead the far portion of wire 56a and near portion of wire 56b may be two discrete portions of wire that terminate at substantially the same spot (e.g., at the break 35) along a fixation member 30a, 30b. In some examples, the two discrete portions of wire may terminate at the break 35 such that a fixation member 30a, 30b that is detached may appear to be a single piece of wire (e.g., it may appear to be contiguous) before a relatively large force is applied upon the respective fixation member 30a, 30b and causes the discrete portions of a fixation member 30a, 30b that is detached to separate at the break 35. In some examples, a fixation member 30a, 30b that is detached may encounter relatively less strain upon the discrete wire portions as a result of being detached.

As is depicted in FIG. 5, the asymmetric loop 50a may be formed having a maximum pitch P1 that is of a lesser magnitude than a maximum pitch P2 of the asymmetric loop 50b. As used herein, a maximum pitch of a loop is the pitch of the largest magnitude of the respective loop. The pitch of loop 50a decreases in a direction towards the junction 52 along a longitudinal axis 26 of the sensor assembly 10a (or increases in a direction away from the junction 52). Similarly, the pitch of loop 50b decreases in a direction towards the junction 52 along a longitudinal axis 26 of the sensor assembly 10 (or increases in a direction away from the junction 52). In examples having more than two loops, each of the additional loops may likewise be formed with decreasing pitches, relative to a junction 52 of such additional loop(s) to one of the adjoining loop(s).

In some examples, the maximum pitches P1, P2 may be configured to improve a fit of the fixation members 30a, 30b in the blood vessel. For example, P2, being larger than P1, may be configured to be slightly greater (e.g., 10% more) than the height of the respective blood vessel that the sensor 10 assembly may be implanted in, such that the fixation members 30a, 30b engage with but do not pierce/push through the walls of the blood vessel. Further, the radius of the wires of the fixation members 30a, 30b may be as large as possible (e.g., while maintaining shape memory and proper alignment) to minimize loading on the capsule 34 and therein the sensor 12.

The fixation members 30a, 30b are each coupled to the capsule 34 at a segment of the first loop 50a. As such, the fixation members 30a, 30b may be coupled to the capsule 34 such that the pitch of the first loop 50a decreases along a longitudinal axis 26 of the housing towards the junction 52. In some examples, the pitch of the first loop 50a increases for a relatively short distance 46a-b (collectively "distances 46") along the longitudinal axis before the pitch decreases. Conversely, the pitch of the second loop increases along the longitudinal axis 26 away from the junction 52. Moreover, the fixation members 30a, 30b may be compressible along a dimension defining the pitch of the first loop 50a and second loop 50b such that each member is collapsible to a reduced pitch in a delivery configuration and expanded to an magnified pitch in a deployment configuration.

In some examples, some or all of the wire of the fixation assembly may be coated (e.g., coated for insulation purposes) or otherwise covered with paralyne or another insulating material. In other examples, wires of the fixation members 30a, 30b may be exposed (e.g., without an electrical insulator around all or part of the conductor of a wire) to create electrical contact with tissue of the patient 2. The fixation members 30a, 30b may be configured to make electrical contact with tissue of the patient 2 in order to transmit signals through the tissue of a patient 2 (e.g., signals to a medical device 16 or a programmer 14 or an external receiver 24). In some examples, wires may be stripped after the maximum pitch P1 of the first loops 50a. Put differently, in some examples, all of the wire of the fixation members 30a, 30b may be stripped with the exception of the wire within the distances 46 of the capsule 34. In such cases, stripping the wires after the maximum pitch P1 of the first loops 50a may provide transmission strength benefits to the sensor assembly 10.

The fixation assembly 30 may stably position the sensor 12 to achieve stable and durable sensing parameters. Further, the fixation assembly 30 may reduce the loads that are transferred by the fixation assembly 30 to the sensing element 32. In some examples, the sensing element 32 is a deformable pressure membrane. Reducing the loads that are transferred to the sensing element may be achieved by providing a fixation assembly 30 having a multi-loop configuration such that at least one of the loops provides strain relief for coupling to the capsule 34 while a second of the loops provides the fixation to maintain the positional integrity of the sensor 12 at the desired implant location. In some examples, the fixation assembly 30 can be constructed such that an outer perimeter of each of the fixation members 30a, 30b is aligned with a plane defined by an exterior portion of the capsule 34. Such a plane can be defined by the bottom longitudinal section of capsule 34 as shown in FIG. 5. In some examples, an arrangement enables the bottom of the capsule 34 to be in contact or adjacent to the wall of the vessel during use while positioning the sensor in the blood flow path within the vessel. Such a construction also provides for unobstructed passage of a guidewire within the lumen of the delivery tool during the implantation of the sensor assembly 10.

In the illustrative example, the fixation members 30a, 30b are coupled at two separate locations on opposing ends of the capsule 34. This provides transverse stability of the capsule 34. In some examples, coupling the fixation members 30a, 30b to the two opposing ends of capsule 34 may provide a fixation structure with a decreasing pitch in opposing directions, which further minimizes the load transfer to the sensing element 32. Furthermore, although the direction of the coupling of fixation assembly 30 is depicted as being parallel with the longitudinal axis of the capsule 34, it should be understood that alternative examples may selectively couple the fixation assembly 30 in a different orientation relative to the capsule 34. For example, the fixation assembly 30 may be coupled perpendicular to the longitudinal axis 26 of the capsule 34.

Figure 7A:
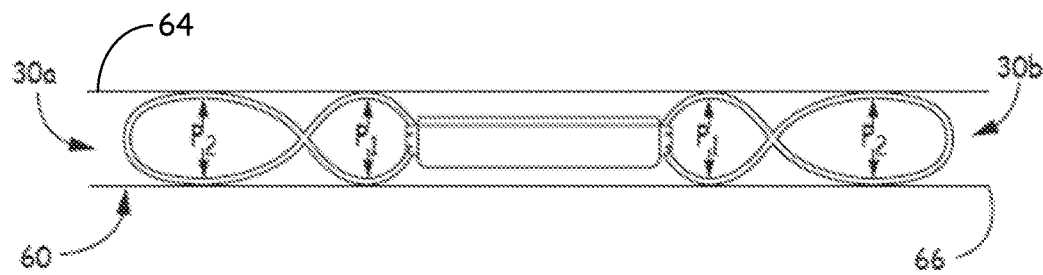
FIG. 7A depicts, diagrammatically and in fragmented illustration, an example sensor assembly in conjunction with an example delivery system.
Figure 7B:
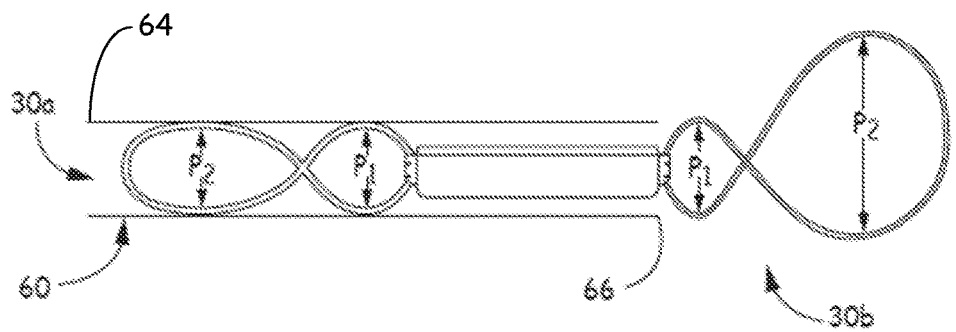
FIG. 7B depicts, diagrammatically and in fragmented illustration, an example sensor assembly in conjunction with an example delivery system.
Figure 7C:
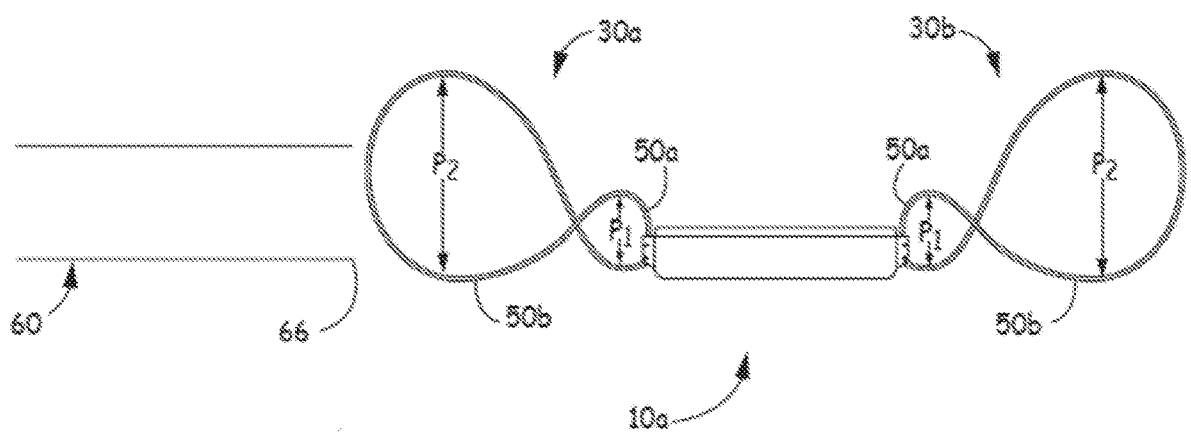
FIG. 7C depicts, diagrammatically and in fragmented illustration, an example sensor assembly in conjunction with an example delivery system.

FIGS. 7A-7C depict, diagrammatically and in fragmented illustration, the sensor assembly in conjunction with an example delivery system that may be used to deliver and deploy the sensor assembly in a desired implant location. The fixation members 30a, 30b are formed from a flexible material that enables the fixation assembly 30 to be compressed to a narrower shape having a smaller effective cross section in which it may be mounted to and delivered by a delivery catheter 60 to an intended implant location such as the pulmonary artery.

In one configuration, the larger of the loops 50 of each of the fixation members 30a, 30b is compressed from its relaxed, expanded deployment configuration to a narrower, more elongated delivery configuration defined by loop segments that are drawn more closely parallel to each other. In this respect, forming fixation members 30a, 30b from a superelastic material (e.g., such as superelastic nitinol, which has the ability to undergo extreme strain without permanent deformation) reduces the risk of permanent deformation when the loops are compressed. Nevertheless, other materials such as stainless steel or plastic may suitably be used to form the fixation members 30a, 30b. In yet another configuration, each of loops 50 of the fixation members 30a, 30b may be compressed from a relaxed, expanded shape to a narrower, more elongated shape.

Turning to FIGS. 7A-7B, the fixation assembly 30 is shown with the fixation members 30a, 30b in a compressed, delivery configuration profile as may be the case while disposed within the delivery catheter 60. The delivery configuration enables the sensor assembly 10 to be delivered to a desired implant location through a delivery catheter 60. FIG. 7A shows the fixation assembly 30 in a delivery configuration such that at least the dimension along the maximum pitch P2 of the second loop 50b is reduced to define a low profile of fixation members 30a, 30b. Depending on the size of the delivery catheter 60, the fixation assembly 30 may be compressed such that the dimensions of both the maximum pitch P1 of the first loop 50a and the maximum pitch P2 of the second loop 50b are reduced to define a low profile of fixation members 30a, 30b.

In FIG. 7B, the fixation assembly 30 is shown partially retracted from the delivery catheter 60 such that the fixation member 30b is in the expanded, deployment configuration such that the dimension along the maximum pitch P1 of the first loop 50a and/or the maximum pitch P2 of the second loop 50b is expanded to its deployed configuration.

The delivery catheter 60 may be in the form of an elongate tubular shaft 62 having proximal end 64 and distal end 66 with the sensor assembly 10 disposed within a region of the shaft. The shaft 62 may be formed from a material and dimensioned to have sufficient flexibility to be navigated through the patient's vasculature to the intended implant location. The delivery catheter 60 may further include a guide sheath or used in association with a guide wire, as is known to one skilled in the art. The sensor assembly 10 may be releasably retained at the region of the shaft by any suitable arrangement, such as the rotatable helical retention elements described in U.S. Pat. No. 8,864,676.

The delivery catheter 60 may be advanced through a guide sheath that, when retracted, exposes the sensor assembly 10 at a desired implant location. In alternative examples, the delivery catheter 60 may be advanced through an introducer to the desired implant location. Once the distal end 66 is positioned near the implant location, the sensor assembly 10 may be deployed by advancing the distal end 66 to deploy the sensor assembly 10. As the sensor assembly 10 is released it self-expands to its expanded configuration within the target implant location.

In FIG. 7C, the entire sensor assembly 10 is shown in an expanded deployment configuration profile, which typically occurs following release of the fixation members 30a, 30b from the delivery catheter 60. The sensor assembly 10 is typically advanced from the delivery catheter 60 and the expansion of the loop 50b causes the sensor assembly 10 to be securely positioned at the target implant location. Repositioning may be accomplished by advancing the delivery catheter 60 to recapture the fixation members 30a, 30b. The recaptured sensor assembly 10 may then be repositioned and redeployed.

The delivery catheter 60 may be advanced to the target implant location by advancing it through a guide sheath, an introducer, a guide wire in an over-the-wire system, or any other mechanism which is known to those skilled in the art. It should be understood that delivery catheter 60 is only one example of a delivery system for sensor assembly 10. Other types of delivery systems can be utilized, including, for example, mechanisms that are slidably disposed around the sensor assembly 10 to constrain the sensor assembly in its delivery configuration until a pusher mechanism ejects the sensor assembly 10 from the distal end of the catheter. It should be noted that the superelastic construction of the fixation members 30a, 30b enables the fixation members 30a, 30b to be elastically distorted from respective planar expanded shape to a shape adapted to fit onto or within a delivery catheter.

Figure 8:
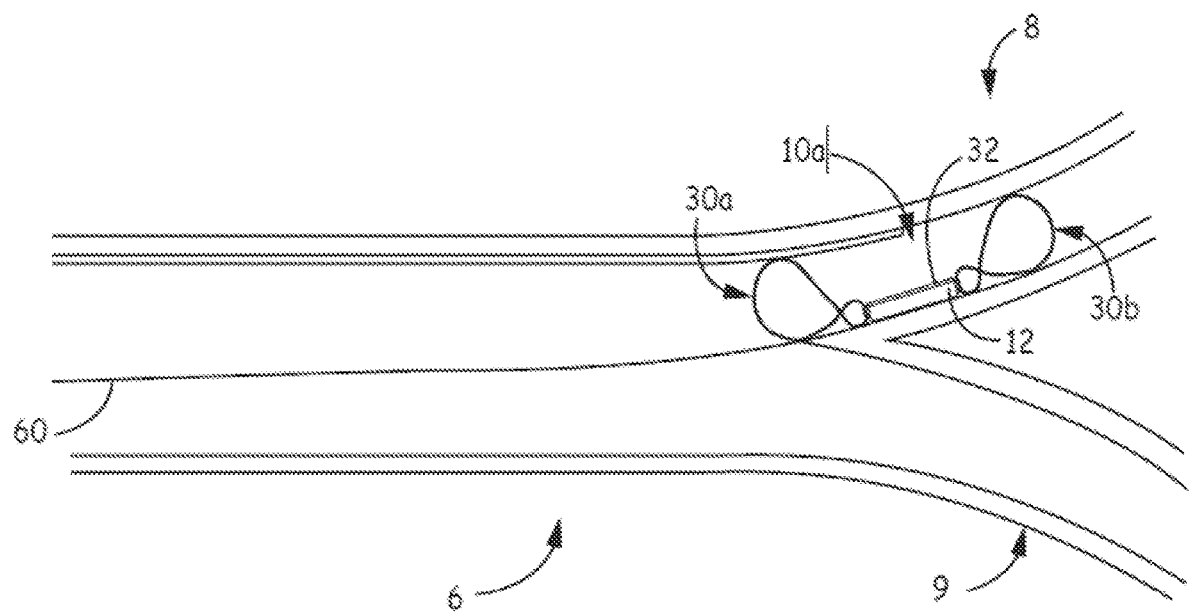
FIG. 8 illustrates, diagrammatically, an example positioning of an example sensor assembly in a target implant location.
Figure 9A:
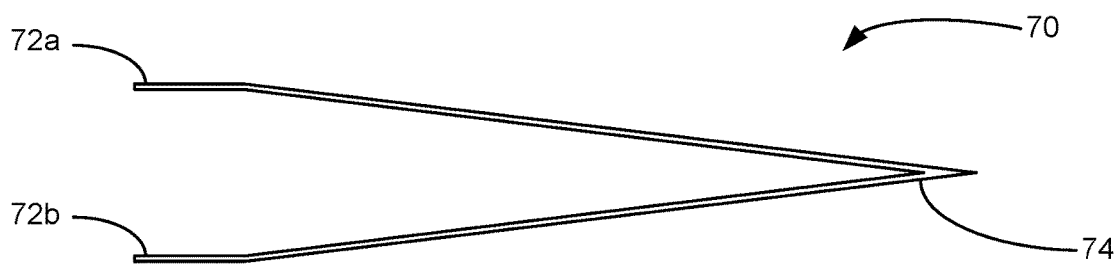
FIG. 9A illustrates a top view of an example fixation assembly for an example sensor assembly.
Figure 9B:
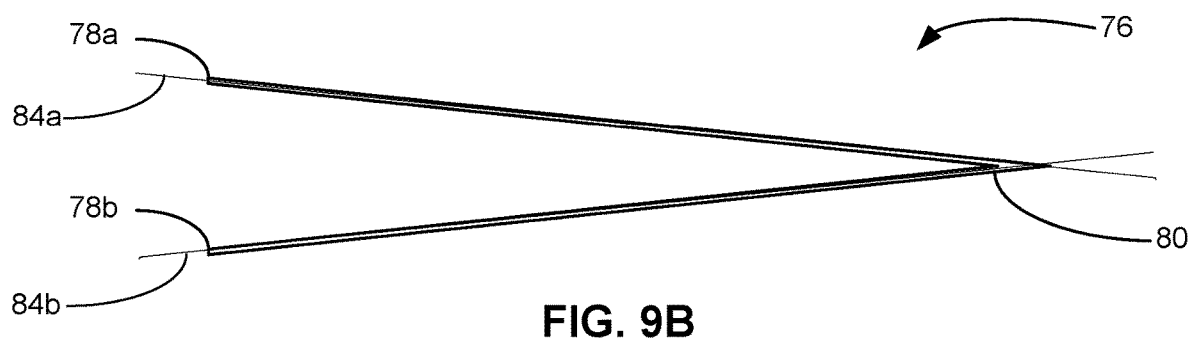
FIG. 9B illustrates a top view of an example fixation assembly for an example sensor assembly.
Figure 9C:
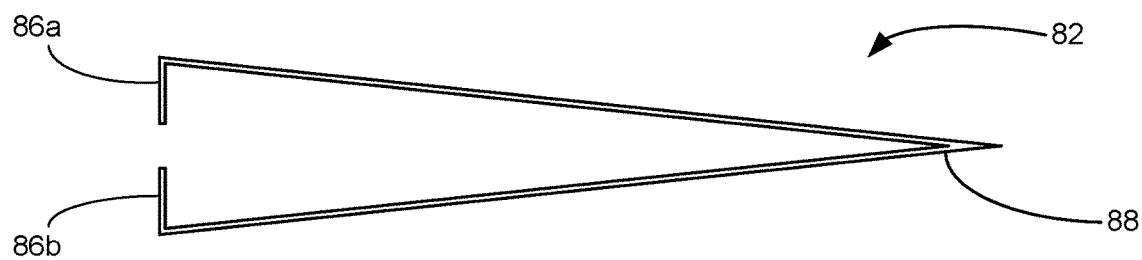
FIG. 9C illustrates a top view of an example fixation assembly for an example sensor assembly.
Figure 9D:
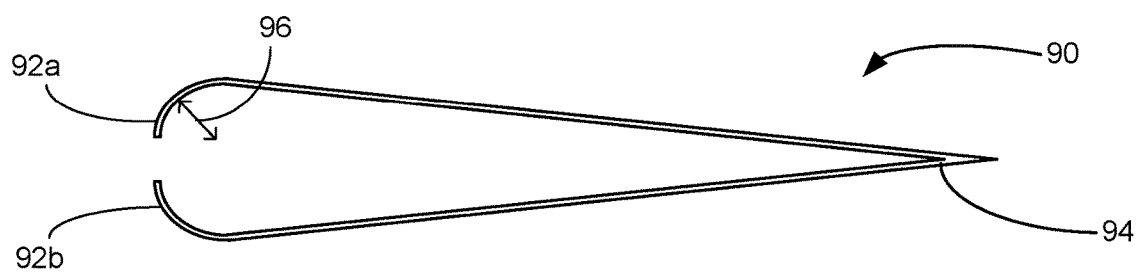
FIG. 9D illustrates a top view of an example fixation assembly for an example sensor assembly.

FIG. 8 illustrates, diagrammatically, the positioning of the sensor assembly 10 in a target implant location. In the depicted example, the implant location is a human pulmonary artery 6, which is generally relatively short and often has a lumen that tapers in the direction of blood flow. The degree of taper may vary from patient to patient, with patients suffering from chronic heart failure tending to have more severe taper with higher pulmonary blood pressures. The main pulmonary artery branches into left and right pulmonary arteries 8, 9. Whether the clinician will elect to place a device in the main artery or one of the branches of the pulmonary artery tree will depend on the anatomy and condition of the particular patient among other factors.

When deploying the sensor assembly 10, the delivery catheter 60 may be positioned so that the more distal of fixation members 30a, 30b will be located in the selected portion of the selected artery. Fixation assembly 30 may apply little more than the force that is required to hold the sensor assembly 10 in place without applying excessive force to that surface. The fixation assembly 30 is constructed to apply light, but sufficient, force to the vessel. Such forces are at least less than those associated with the placement of vascular stents in which the objective is to press against the vascular wall with sufficient force to provide scaffolding support for the vessel wall. By contrast, aspects of the disclosure intend to maintain the sensor assembly 10 in the vessel, without migrating upstream or downstream, while supporting the sensor 12 in its intended position and orientation for measurement of stable and durable sensing parameters. When the sensor assembly 10 is deployed, the fixation members 30a, 30b expand along a single plane with at least one loop of each fixation member 30a and 30b expanding to a dimension to be in contact with the luminal wall of the vessel. Regardless of the orientation of the sensor assembly 10 during delivery, the at least one loop that is in contact with the vessel wall will seat itself at substantially diametrically opposite surfaces of the vessel wall (e.g., at least one loop of each fixation member 30a, 30b may press into both sides of a vessel wall). As used in this disclosure, the term substantially diametrically opposite may mean that the surfaces are opposite one another or within a 15% variance of being opposite each other. Among other things, such a construction can enable the at least one loop to maintain the positional integrity of the sensor assembly 10 with respect to the vessel. In that deployed position, the sensing element 32 may be oriented along a longitudinal axis in relation to the length of the vessel lumen to be exposed fully and without obstruction to blood flow in the lumen.

In other examples, the fixation assembly and sensor are arranged such that the sensing element faces generally parallel to the plane of the fixation assembly. The fixation assembly also may be configured to position the sensor housing and, particularly, the sensing element, away from the vessel wall to lessen the risk of turbulent flow through the vessel.

FIGS. 9A-D illustrate top views of example fixation members 70, 76, 82, 88 for an example sensor assembly (not depicted). FIGS. 9A-D depicts fixation members 70, 76, 82, 88 from the same view as FIG. 3A. Fixation members 70, 76, 82, 88 includes an angled portion 74, 80, 86, 92 (respectively) and free ends for connecting the respective fixation members 70, 76, 82, 88 to respective capsules 34. The specific angles of the fixation members 70, 76, 82, 88 are depicted for purposes of illustration only, other angles and configurations are also possible. For example, in some instances, fixation members 70, 76, 82, 88 could have a more acute angle similar to the angle depicted in FIG. 3A. The fixation members 70, 76, 82, 88 may have two loops, three loops, or more than three loops.

Fixation member 70 includes an angled portion 74 and free ends 72a-b (collectively "free ends 72"). The free ends 72 may be parallel with an axis 26 of the sensor assembly 10. The amount of the fixation assembly 70 that is comprised of the free ends 72 is for example purposes only; in other examples, the free ends 72 may comprise a smaller or larger overall amount of the fixation member 70. The free ends 72 may connect to the capsule 34 as described herein. In some examples, it may be easier to attach the fixation member 70 to the capsule 34 due to the free ends 72 lining up with relative components (e.g., fasteners) of the capsule 34.

Fixation member 76 includes an angled portion 80 and two free ends 78a-b (collectively "free ends 78"). The free ends 78 may be parallel with planes 84a-b (collectively "planes 84") of the fixation member 76. Planes 84 of the fixation member 76 may be substantially similar to planes 44 of the fixation members 30a, 30b as described herein. The free ends 78 may connect to a capsule 34 as described herein. In some examples, fixation member 76 may experience benefits in balancing loads throughout the fixation assembly 76 being as there are no turns in transitioning to the free ends 78 (as seen from the top) in which loads may be concentrated. Further, in certain examples, it may be easier/less expensive to manufacture fixation member 76 than other fixation members, as less turns are required.

Fixation member 82 includes an angled portion 88 and free ends 86a-b (collectively "free ends 86"). The length of the free ends 86 is for example purposes only; in other examples, the free ends 86 may be longer or shorter. The free ends 86 may connect to the capsule 34 as described herein. The free ends 86 may parallel to a respective lateral sidewall SW1, SW2 of the capsule 34. In some examples, it may be easier to attach the fixation member 82 to the capsule 34 due to the free ends 86 lining up correctly with relative components (e.g., fasteners) of the capsule 34. Further, in some examples, loads upon the angled portion 88 may be relatively lower, as loads do not transfer efficiently from the free ends 86 to the angled portion 88 due to the free ends being parallel with a respective lateral wall SW1, SW2.

Fixation member 90 includes an angled portion 94 and free ends 92*a-b* (collectively "free ends 92"). The length and angle of the free ends 92 is for example purposes only; in other examples, the free ends 92 may be longer or shorter at different angles. The free ends 92 may connect to the capsule 34 as described herein. The free ends 92 may curve into the capsule with a radius 96. In some examples, loads upon the angled portion 94 may be relatively lower, as loads do not transfer efficiently from the free ends 92 to the angled portion 94 due to the curve with the radius 96.

Figure 10:
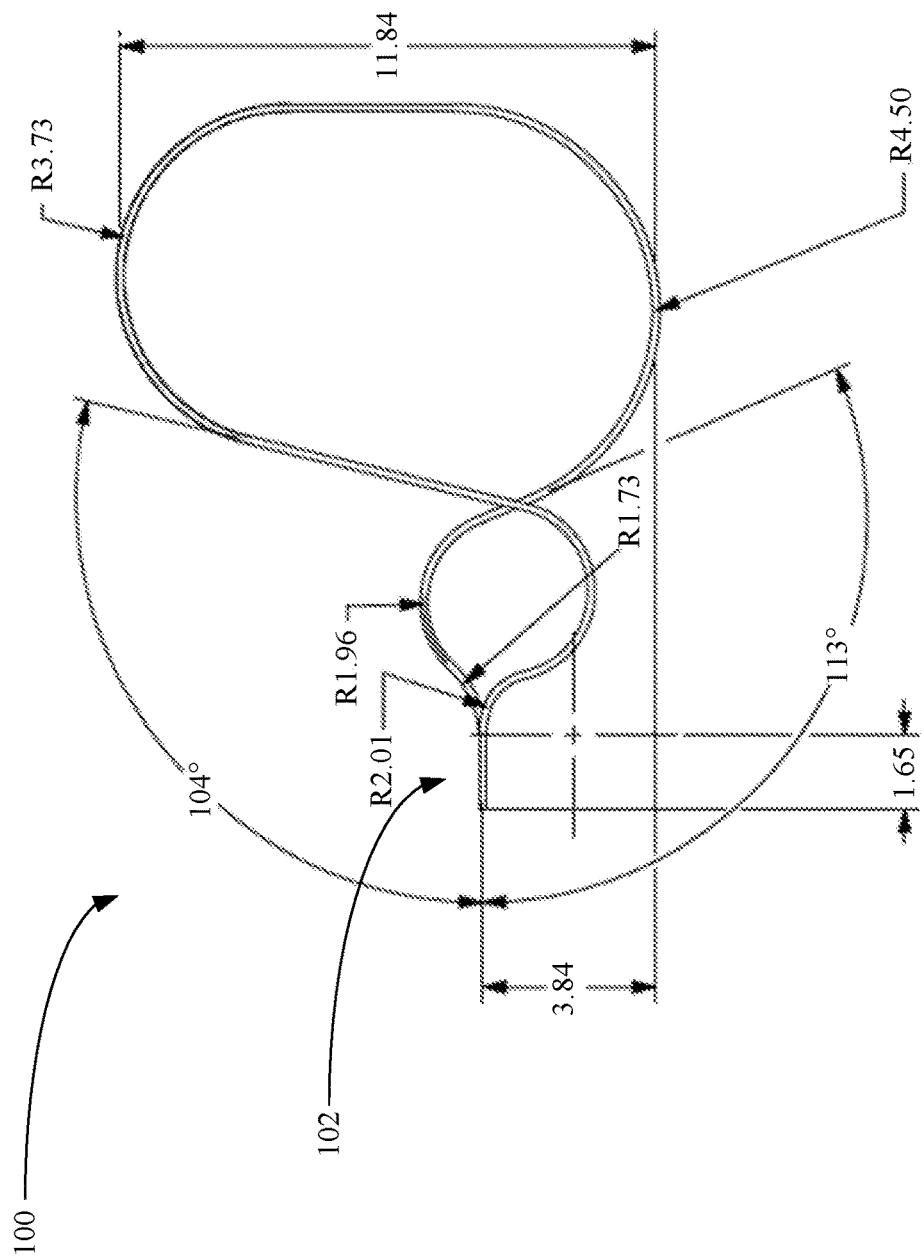
FIG. 10 illustrates a side profile view of an example fixation assembly for an example sensor assembly.

FIG. 10 illustrates a side profile view of an example fixation member 100 for an example sensor assembly (not depicted). All dimensions are in millimeters and are for purposes of example only; other dimensions consistent with this disclosure are also possible. A connection portion 102 of the fixation member 100 may incorporate any of the connection configurations discussed in FIGS. 9A-9D.

FIG. 11 illustrates a side profile view of example configurations of a fixation member 110 for an example sensor assembly (not fully depicted). Fixation member 110 may attach to a capsule 34 as depicted. In other examples, fixation member attaches to a capsule 34 in other manners consistent with this disclosure (e.g., as depicted in FIG. 4A). Fixation member 110 has a first loop 124 and a second loop 126. In other examples, fixation member 110 has more than two loops as described above.

A first loop 124 of the fixation member 110 may be configured with any one of a plurality of maximum pitches 120*a-d* (collectively "maximum pitches 120"). The first loop 124 may be configured with to have one of a plurality of maximum pitches 120 as a result of altering arrangements of far portions of wire 58 that is closer to longitudinal side wall LS2 than longitudinal side wall LS1. The far portion of wire 58 may be arranged differently immediately upon extending axially out from the capsule 34. For example, the far portion of wire 58 may be arranged in the arrangements 112, 114, 116, 118 depicted in FIG. 11. In other examples, the fixation member 110 may be arranged in other manners that are consistent with this disclosure (e.g., the far portion of wire 58 may arranged to occupy space between arrangement 114 and arrangement 118).

In some examples, an arrangement 112 of the far portion of wire 58 may include the far portion of wire 58 rising up (e.g., moving axially out from the capsule 34 in the general direction of the longitudinal wall LW1 relative to the capsule 34) such that the pitch of the first loop 124 increases relatively quickly to a maximum pitch 120*a* and then decreases to the juncture 52. In other examples, an arrangement 116 of the far portion of wire 58 may include the far portion of wire 58 rising up relatively moderately such that the pitch of the first loop 124 increases to a to a maximum pitch 120*b* (e.g., where maximum pitch 120*b* is less than maximum pitch 120*a*) and then decreases to the juncture 52. In other examples, an arrangement 118 of the far portion of wire 58 may include the far portion of wire 58 dipping down (e.g., moving axially in the general direction of the longitudinal wall LW2 relative to the capsule 34) before rising slightly to the maximum pitch 120*c* (e.g., where maximum pitch 120*c* is less than maximum pitch 120*b*), such that the pitch of the first loop 124 slightly increases until the maximum pitch 120*c* and then slightly decreases until the juncture. In other examples, an arrangement 114 of the far portion of wire 58 may dip down at a slower rate than the near portion of wire 56 dips down, such that the first loop 124 has a maximum pitch of 120*d* (e.g., where the maximum pitch 120*d* is less than the maximum pitch 120*c*).

In some examples, a larger maximum pitch 120 of the first loop 124 may provide more stiffness to the fixation assembly 124. For example, arrangement 112 may be relatively more stiff than arrangement 116 (e.g., as maximum pitch 120*a* is larger than maximum pitch 120*b*), while arrangement 116 is relatively more stiff than arrangement 118, while arrangement 114 is relatively more stiff than arrangement 118. In such examples, it may be advantageous for a fixation member 110 to be stiff enough to maintain a shape and engage walls of a blood vessel while not being so stiff as to immediately or eventually push through walls of a blood vessel. As such, different arrangements 112, 114, 116, 118 may be utilized for different applications depending upon the stiffness required for the specific parameters of the respective application.

The following paragraphs include examples (enumerated consecutively from 1 to 34) that provide for various aspects of the present disclosure. In one example of a first paragraph (1), an implantable medical device comprises:

a housing including a power source, a sensing element, and an electronic circuit configured to generate a signal indicative of a physiological parameter measured by the sensing element, the housing having first and second opposing ends; and a fixation assembly including asymmetric fixation members coupled to the opposing ends of the housing, wherein each of the asymmetric fixation members includes a structure with a plurality of loops, wherein a first loop of the plurality of loops has a maximum pitch that is different from a maximum pitch of a second loop of the plurality of loops.

2. The implantable medical device of paragraph 1, wherein each loop of the structure is formed in a helical configuration.

3. The implantable medical device of any of paragraphs 1-2, wherein the first loop is coupled to the housing such that a pitch of the first loop increases from the junction towards the housing and a pitch of the second loop increases in a direction away from the junction.

4. The implantable medical device of any of paragraphs 1-3, wherein each of the asymmetric fixation members is configured in a figure-of-eight structure with each of the loops of the figure-of-eight structure having a different maximum pitch.

5. The implantable medical device of any of paragraphs 1-4, wherein each of the asymmetric fixation members is configured to contact the walls of a blood vessel along a plurality of planes.

6. The implantable medical device of any of paragraphs 1-5, wherein each plane of the plurality of planes is perpendicular to a surface of the capsule to which the fixation members are affixed.

7. The implantable medical device of any of paragraphs 1-6, wherein each of the fixation members includes first and second free ends, wherein the first and second free ends are parallel with a plane of the plurality of planes.

8. The implantable medical device of any of paragraphs 1-7, wherein the asymmetric fixation members have opposite arrangements as reflected across a central plane of the implantable medical device.

9. The implantable medical device of any of paragraphs 1-8, wherein at least one loop of the structure is dimensioned having a diameter to contact a portion of a wall of a vessel to thereby maintain the pressure sensor at a fixed location within the vessel.

10. The implantable medical device of any of paragraphs 1-9, wherein the vessel is a pulmonary artery.

11. The implantable medical device of any of paragraphs 1-10, wherein a pitch of each loop increases from the junction along an axis that is parallel to a longitudinal axis of the housing.

12. The implantable medical device of any of paragraphs 1-11, wherein the sensing element is a pressure membrane and the measured physiological parameter is blood pressure.

13. The implantable medical device of any of paragraphs 1-12, wherein the housing further comprises an electronic circuit configured to generate a signal indicative of the physiological parameter measured by the sensing element.

14. The implantable medical device of any of paragraphs 1-13, wherein the structure has a variable pitch such that the fixation assembly is compressible in a delivery configuration and expandable into a deployment configuration that is different from the delivery configuration.

15. The implantable medical device of any of paragraphs 1-14 wherein each of the fixation members includes first and second free ends with the first free ends of the fixation members being oriented in opposing directions relative to one other and the second free ends of the fixation members being oriented in opposing directions relative to one other.

16. The implantable medical device of any of paragraphs 1-14, wherein each of the fixation members includes first and second free ends, wherein the first and second free ends are parallel with a longitudinal axis of the implantable medical device.

17. The implantable medical device of any of paragraphs 1-14, wherein each of the fixation members includes first and second free ends, wherein the first and second free ends are perpendicular with a longitudinal axis of the implantable medical device.

18. The implantable medical device of any of paragraphs 1-17, wherein a surface of the housing that contacts a wall of a blood vessel is sintered.

19. An implantable medical system, comprising:
- a physiological sensor including:
  - a housing including a power source, a sensing element, and an electronic circuit configured to generate a signal indicative of a physiological parameter measured by the sensing element, the housing having first and second opposing ends; and
  - a fixation assembly including asymmetric fixation members coupled to the opposing ends of the housing, wherein each of the asymmetric fixation members includes a structure with a plurality of loops, wherein a first loop of the plurality of loops has a maximum pitch that is different from a maximum pitch of a second loop of the plurality of loops; and
- a delivery catheter having an elongate body for delivery of the physiological sensor.

20. The implantable medical device of paragraph 19, wherein the sensing element is a pressure membrane and the measured physiological parameter is blood pressure.

21. The implantable medical device of any of paragraphs 19-20, wherein each loop of the structure is formed in a helical configuration.

22. The implantable medical device of any of paragraphs 19-21, wherein each of the asymmetric fixation members is configured in a figure-of-eight structure with each of the loops of the figure-of-eight structure having a different maximum pitch.

23. The implantable medical device of any of paragraphs 19-22, wherein at least one loop of the structure is dimensioned having a diameter to contact a portion of a wall of a vessel to thereby maintain the pressure sensor at a fixed location within the vessel.

24. The implantable medical device of paragraph 23, wherein the vessel is a pulmonary artery.

25. The implantable medical device of any of paragraphs 19-24, wherein the housing further comprises an electronic circuit configured to generate a signal indicative of the physiological parameter measured by the sensing element.

26. The implantable medical device of any of paragraphs 19-25, wherein each of the fixation members includes first and second free ends with the first and second free ends being oriented in opposing directions relative to one other.

27. The implantable medical device of any of paragraphs 19-26, wherein the structure has a variable pitch such that the fixation assembly is compressible in a delivery configuration while the physiological sensor is disposed within the delivery catheter and expandable into a deployment configuration that is different from the delivery configuration responsive to withdrawal of the physiological sensor from the delivery catheter.

28. The implantable medical device of any of paragraphs 19-27, wherein each of the asymmetric fixation members is configured to contact the walls of a blood vessel along a plurality of planes.

29. The implantable medical device of paragraph 28, wherein each plane of the plurality of planes is perpendicular to a surface of the capsule to which the fixation members are affixed.

30. The implantable medical device of any of paragraphs 19-29, wherein each of the fixation members includes first and second free ends, wherein the first and second free ends are parallel with a plane of the plurality of planes.

31. The implantable medical device of any of paragraphs 19-29, wherein each of the fixation members includes first and second free ends, wherein the first and second free ends are parallel with a longitudinal axis of the implantable medical device.

32. The implantable medical device of any of paragraphs 19-31, wherein a surface of the housing that contacts a wall of a blood vessel is sintered.

33. The implantable medical device of any of paragraphs 19-32, wherein the asymmetric fixation members have opposite arrangements as reflected across a central plane of the implantable medical device.

34. An implantable medical device, comprising:
- a housing having first and second opposing ends;
- a pressure sensing element on the housing;
- an electronic circuit within the housing, the electronic circuit coupled to the pressure sensing element and configured to generate a signal indicative blood pressure; and
- a fixation assembly including a first asymmetric fixation member coupled to the first opposing end of the housing and a second asymmetric fixation member coupled to the second opposing end of the housing,
  wherein each of the asymmetric fixation members includes a structure with a first loop and a second loop, the first loop more proximate to the housing than the second loop,
  wherein the first loop has a maximum pitch less than a maximum pitch of the second loop, and
  wherein each of the fixation members includes first and second free ends with the first free ends of the fixation members being oriented in opposing directions relative to one other and the second free ends of the fixation members being oriented in opposing directions relative to one other.

What is claimed is:

1. An implantable medical device configured to position within a blood vessel, the implantable medical device comprising:
   a housing including a power source, a sensing element, and an electronic circuit configured to generate a signal indicative of a physiological parameter measured by the sensing element; and
   a fixation assembly configured to be expandable in the blood vessel from a delivery configuration to a deployment configuration, the fixation assembly including a fixation member coupled to an end of the housing, wherein the fixation member includes a first loop and a second loop, wherein the first loop and the second loop are configured to position the housing adjacent a wall of the blood vessel when the fixation assembly expands to the deployment configuration, and wherein the first loop defines a first double helical configuration and the second loop defines a second double helical configuration.

2. The implantable medical device of claim 1, wherein the first loop and the second loop are configured to contact the wall of the blood vessel when the fixation assembly expands to the deployment configuration.

3. The implantable medical device of claim 1, wherein the housing defines a top longitudinal wall and a bottom longitudinal wall opposite the top longitudinal wall, wherein the sensing element is supported by the top longitudinal wall, and wherein the fixation assembly is configured to position the bottom longitudinal wall adjacent the wall of the blood vessel when the fixation assembly expands to the deployment configuration.

4. The implantable medical device of claim 1, wherein:
   the fixation member is a first fixation member and the end of the housing is a first end of the housing,
   the fixation assembly includes a second fixation member coupled to a second end of the housing opposite the first end, and
   the second fixation member is configured to position the housing adjacent the wall of the vessel when the first loop and the second loop position the housing adjacent the wall of the vessel.

5. The implantable medical device of claim 4, wherein the first fixation member and the second fixation member are configured to contact the wall of the blood vessel when the fixation assembly expands to the deployment configuration.

6. The implantable medical device of claim 1, wherein the fixation member is configured to occupy a plurality of planes when the fixation assembly expands to the deployment configuration, wherein the plurality of planes are configured to resist a twisting of the housing in a direction perpendicular to one of the planes.

7. The implantable medical device of claim 1, wherein the fixation member includes a linear element configured to form the first loop and the second loop.

8. The implantable medical device of claim 1, wherein the fixation member overlaps at a first junction to form the first loop and overlaps at a second junction to form the second loop.

9. The implantable medical device of claim 8, wherein a first pitch of the first loop increases from the first junction in a direction away from the first junction, and wherein a second pitch of the second loop increases from the second junction in a direction away from the second junction.

10. The implantable medical device of claim 1, wherein the fixation member includes a first free end and a second free end, and wherein the fixation member is configured to form the first loop and the second loop between the first free end and the second free end.

11. The implantable medical device of claim 1, wherein the implantable medical device defines a first channel and a second channel, and wherein the fixation member is configured to define the first loop and the second loop when a first segment of the fixation member is received in the first channel and a second segment of the fixation member is received in the second channel.

12. The implantable medical device of claim 11, wherein the housing includes a first longitudinal wall and a second longitudinal wall defining a longitudinal axis, and wherein at least one of a first free end of the first segment or a second free end of the second segment are substantially perpendicular to the longitudinal axis when the first segment is received in the first channel and the second segment is received in the second channel.

13. The implantable medical device of claim 1, wherein the implantable medical device is configured to position within a pulmonary artery.

14. The implantable medical device of claim 1, wherein the electronic circuit is configured to generate a signal indicative of the physiological parameter measured by the sensing element.

15. The implantable medical device of claim 1, wherein the first loop and the second loop are configured to position a surface of the housing adjacent the wall of the blood vessel, and wherein the surface of the housing is sintered.

16. The implantable medical device of claim 1, wherein the sensing element is a pressure membrane and measured physiological parameter is a blood pressure.

17. An implantable medical device configured to position within a blood vessel, the implantable medical device comprising:
   a housing including a power source, a sensing element, and an electronic circuit configured to generate a signal indicative of a physiological parameter measured by the sensing element; and
   a fixation assembly configured to be expandable in the blood vessel from a delivery configuration to a deployment configuration, the fixation assembly comprising:
      a first fixation member coupled to a first end of the housing, wherein the first fixation member includes a first loop and a second loop; and
      a second fixation member coupled to a second end of the housing opposite the first end,
      wherein the first loop, the second loop, and the second fixation member are configured to contact a wall of the blood vessel when the fixation assembly expands to the deployment configuration, such that the first loop, the second loop, and the second fixation member position the housing adjacent the wall of the blood vessel when the fixation assembly expands to the deployment configuration, and
      wherein the first loop defines a first double helical configuration and the second loop defines a second double helical configuration.

18. The implantable medical device of claim 17, wherein the first fixation member includes a linear element configured to overlap at a first junction to form the first loop and overlap at a second junction to form the second loop.

19. The implantable medical device of claim 17, wherein the implantable medical device defines a first channel and a second channel, and wherein the first fixation member is configured to define the first loop and the second loop when a first segment of the first fixation member is received in the first channel and a second segment of the first fixation member is received in the second channel.

20. The implantable medical device of claim 17, wherein the housing defines a top longitudinal wall and a bottom longitudinal wall opposite the top longitudinal wall, wherein the sensing element is supported by the top longitudinal wall, and wherein the fixation assembly is configured to position the bottom longitudinal wall adjacent the wall of the blood vessel when the fixation assembly expands to the deployment configuration.

* * * * *